United States Patent [19]
Bae et al.

[11] Patent Number: 5,687,208
[45] Date of Patent: Nov. 11, 1997

[54] METHOD OF AND APPARATUS FOR PREDICTING COMPUTED TOMOGRAPHY CONTRAST ENHANCEMENT WITH FEEDBACK

[75] Inventors: Kyongtae T. Bae; Jay P. Heiken; James A. Brink, all of St. Louis, Mo.

[73] Assignee: BHB General Partnership, St. Louis, Mo.

[21] Appl. No.: 648,495

[22] Filed: May 15, 1996

Related U.S. Application Data

[63] Continuation-in-part of Ser. No. 539,859, Oct. 6, 1995, Pat. No. 5,583,902.

[51] Int. Cl.⁶ .................................................. A61B 6/03
[52] U.S. Cl. .......................... 378/8; 378/901; 364/413.15
[58] Field of Search ........................ 364/413.15, 413.14; 378/8, 95, 901

[56] References Cited

U.S. PATENT DOCUMENTS

| | | | |
|---|---|---|---|
| 5,301,672 | 4/1994 | Kalender | 128/654 |
| 5,459,769 | 10/1995 | Brown | 378/4 |
| 5,583,902 | 12/1996 | Bae | 378/8 |

OTHER PUBLICATIONS

Lars Kopka, M.D., et al., Dual–phase Helical CT of the Liver: Effects of Bolus Tracking and Different Volumes of Contrast Material, Radiology vol. 201, No. 2, Nov. 1996, pp. 321–326.

Dynamic Hepatic CT: How Many Years Will It Take 'Til We Learn? Walkey, MM. Radiology vol. 1, Oct., 1991: 181:17–24.

Investigation of Contrast Enhancement In CT Of The Liver: The Need For Improved Methods, Dodd, GD, Baron, TL. (commentary). AJR 1993: 160:643–646.

Contrast–Enhanced Spiral CT Of The Liver: Effect Of Different Amounts And Injection Rates Of Contrast Material On Early Contrast Enhancement. Small, WC, Nelson, RC, Bernadino, ME, Brummer, LT. AJR 1994: 163–87–92.

Cardiac Output And Regional Blood Flow, Wade OL, Bishop, JM. F.A. Davis Co., Philadelphia, 1962, pp. 86–95.

(List continued on next page.)

*Primary Examiner*—David P. Porta
*Assistant Examiner*—David Vernon Bruce
*Attorney, Agent, or Firm*—Howell & Haferkamp, L.C.

[57] ABSTRACT

A method and apparatus are disclosed for predicting prior to injection an organ specific contrast enhancement in a patient for a preselected contrast injection protocol for pre-determining a computed tomography scan. The invention is preferably implemented in a computer program which creates a mathematical model of human cardiovascular physiology in a hypothetical patient with a specific body habitus subjected to the pre-selected contrast injection protocol. The predicted contrast enhancement is then displayed for operator approval and may be then used to control a CT scanner or contrast injector system, to perform the injection and scan with the pre-selected injection protocol and scan parameters. The mathematical model includes models of organs and vessels using differential equations to describe mass transport of contrast agent through the cardiovascular system. Also disclosed are a method and apparatus for predicting optimum injection protocol for contrast agent by analyzing the predicted enhancement levels and updating the injection protocol until acceptable enhancement levels are predicted as well as a method and apparatus for determining an optimum scan interval when enhancement levels are predicted to exceed a threshold level for a time period greater than the scan duration. Further disclosed is a method and apparatus for monitoring a region of interest in the patient different from the region to be scanned after injection to calibrate the mathematical model and more accurately predict enhancement levels in the tissue to be scanned and calculate the optimum scan parameters.

38 Claims, 20 Drawing Sheets

OTHER PUBLICATIONS

Cardiovascular Physiology. Milnor, WR. *Oxford University Press*, Oxford, 1990. pp. 6–13; 28–39; 52–59; 328–331; 436–445.

Structure–Function Relations In The Peripheral Circulation; *Best & Taylor's Physiological Basis of Medical Practice;* Twelfth Edition; Chapter 6, pp. 118–123; 128–130; and 142; Chapter 25; Physiology Of The Body Fluids, pp. 406–408, edit by West, JB., Williams & Wilkins, 1991.

Circulation–Time Models Of The Uptake Of Inhaled Anaesthetics And Data For Quantifying Them. Mapleson, WW. *Brit J. Anaesth,* 1973; 45:319–333.

Summary of Organ Weight (g) For Pediatric And Adult Phantoms. *CRC Handbook of Medical Physics.* ICRP Publication 23, 1984. pp. 428, 134–135.

Local Control of Blood Flow by the Tissues and Nervous and Humoral Regulation, Textbook of Medical Physiology, Chapter 20. Guyton, AC. WB Saunders Co. 7th Ed. Philadelphia, 1986. pp. 228, 230, 340, 342, Chapter 33, Partition of The Body Fluids: Osmotic Equilibria Between Extracellular And Intracellular Fluids, pp. 382, 384, 386, 388, 390, and 392.

Human Pharmacokinetics Of Iohexol: A New Nonionic Contrast Medium. Olsson B, Aulie A, Sveen K, Andrew E; *Investigative Radiology* Mar.–Apr. 1983; vol. 18, 18:177–182.

Applications Of A Mathematical Model For Drug Distribution In Mammals In Chemical Engineering In Medicine And Biology. Bischoff, KB. Edited by D. Hershey, Plenum Press, NY, 1967; 417–466.

Transport Phenomena in the Cardiovascular System, Middleman, S. John Wiley & Sons, Inc. NY, 1972, pp. 1–299.

Radioisotopes and Circulation. Nadler SB, Hidalgo JU. *Little, Brown& Co.,* Blood Volume. Ch. 4, Boston 1965, pp. 64–71, 86–93.

Numerical Recipes. Chapter 15, Integration of Ordinary Differential Equations. Press WH, Flannery BP, Teukolsy SA, Vetterling WT. *Cambridge University Press,* Cambridge, 1986. pp. 547–561.

Dynamic Contrast–Enhanced CT of the Liver: Comparison of Contrast Medium Injection Rates and Uniphasic and Biphasic Injection Protocols. Heiken JP, Brink JA, McClennan BL, Sagel SS, Forman HP, DiCroce J. *Radiology* May, 1993; 187:327–331.

Dynamic Incremental CT: Effect of Volume and Concentration of Contrast Material and Patient Weight on Hepatic Enhancement. Heiken JP, Brink JA, McClennan BL, Sagel SS, Crowe TM, Gaines MV. *Radiolgoy* May, 1995; 195:353–357.

Extravascular Contrast Material: The Major Component of Contrast Enhancement. Kormano M, Dean PB. *Radiology* Nov., 1976; 121:379–382.

The Permeability of Capillaries in Various Organs as Determined by Use of The 'Indicator Diffusion' Method. Crone, C. *Acta Physiol Scand* 1963; 58:292–305.

Estimation of The Capillary Permeability Coefficients of Inulin in Various Tissues of the Rabbit. Wittmers LE, Bartlett M., Johnson JA. *Microvas Res* 1976; 11:67–78.

A Linear Method for Determining Liver Sinusoidal and Extravascular Volumes. Goresky CA. *American Journal Physiology* 1963; 204(4):626–640.

Capillary Exchange Modeling: Barrier–Limited and Flow-–Limited Distribution. Goresky CA. Ziegler WH, Bach GG. *Circulation Research* Nov., 1970; 27:739–764.

Some Mathematical Aspects Of Chemotherapy–II: The Distribution of a Drug in the Body. Bellman R., Jacquez JA, Kalaba R. *Bull Math Biophys.* 1960; 22:309–322.

Respiration and Circulation; Altman PL, Ditmer DS; *Federation of American Society of Experimental Biology;* Bethesda, MD 1971, pp. 227, 232, 234, 320, 357, 377, 379, 383, 385, 417, 419, 424, 426, 428, 431, 433, 435, 459, 501, 503, 505, 507, 510.

Radiopapque Contrast Media Radiopharmaceuticals Enhancement Agents for Magnetic Resonance Imaging and Ultrasound; Swanson DP, Weingarden M, Swanson DP, Chilton HM, Thrall JH, ed. *Pharmaceuticals in Medical Imaging;* Macmillan Pub. Co. NY, 1990, pp. 78–97.

Circulatory Physiology: Cardiac Output and its Regulation; Guyton AC, WB Saunders Co., Philadelphia, 1963, pp. 3–15, 154–157.

Changes in Cardiac Output With Age; Brandfonbrener M. et al.; Circulation vol. 12; Oct., 1995, pp. 557–566.

Measurement of Cardiac Output by Computed Transmission of Tomography; Herfkens RJ, et al.; Inv. Radiology Nov-–Dec., 1982, pp. 550–553.

Dynamic Contrast Enhancement of the Upper Abdomen: Effect of Contrast Medium and Body Weight; Kormano, M, M.D., Kaarina P., M.D., Soimakallio, S., M.D., Kivimaki, T., RT. *Investigative Radiology,* vol. 18, Jul.–Aug. 1983, pp. 364–367.

Helical CT of the Liver: Clinical Application of an Automated Computer Technique SmartPrep for Obtaining Images With Optimal Contrast Enhancement; Silverman P., Roberts S., Tefft MC., Brown B., Fox SH., Cooper C., Zeman R. *AJR,* Jul., 1995 165:73–78.

Optimal Contrasst Enhancement of the Liver Using Helical (Spiral) CT: Value of SmartPrep; Silverman P., Brown B., Wray H., Fox S., Cooper C., Roberts S., Zeman R.; *AJR* May, 1995; 164:1169–1171.

Technical Developments and Instrumentation. Parenchymal Liver Enhancement With Bolus–Triggered Helical CT: Preliminary Clinical Results; Kopka L., Funke M., Fischer U., Vosshenrich R., Oestmann JW., Grabbe E. *Radiology* Apr., 1995, vol. 195, No. 1, pp. 282–284.

Application of Pharmacokinetics to Computed Tomography Injection Rates and Schemes: Mono–, Bi–, or Multiphasic; Werner Kraus, PhD.; *Investigative Radiology,* Feb. 1996, vol. 31, pp. 91–100.

*Fundamentals of Special Radiographic Procedures;* Albert M. Snopek; Third Edition, Automatic Injection Devices; Chapter 3, pp. 38–65.

*Fundamentals of Angiography,* Tortorici M.; 1982, Automatic Injectors; Chapter 5, pp. 69–80.

Assessment of a Technology That Permits Individualized Scan Delays on Helical Hepatic CT: a Technique to Improve Efficiency in Use of Contrast Material, Silverman, P., et al.; *AJR:*167, Jul. 1996, pp. 79–84.

Helical CT of the liver: Evaluating the onset and slope of hepatic enhancement as parameters for scan initiation utilizing a semi–automated scan delay; Abstract Form presented at Society of Computed Body Tomography and Magnetic Resonance Scientific Session in Scottsdale, Arizona; Mar. 17, 1995.

Medrad Mark V Plus Injector Operation Manual KMP 805 P for systems, SYS500–P, RMP 505–P/510–P, SYS500–ESP and CRM255; 1990.

Enhancement (H.U.)

| TIME (MIN.) | AORTIC | HEPATIC |
|---:|---:|---:|
| 0 | 0 | 0 |
| 0.13 | 16.23 | 0.02 |
| 0.25 | 187.3 | 3.12 |
| 0.38 | 285.65 | 15.53 |
| 0.51 | 324.22 | 34.8 |
| 0.64 | 176.9 | 52.39 |
| 0.77 | 135.62 | 60.29 |
| 0.91 | 127.09 | 62.9 |
| 1.04 | 127.15 | 63.57 |
| 1.17 | 122.31 | 63.57 |
| 1.3 | 114.23 | 63 |
| 1.43 | 108.87 | 61.84 |
| 1.56 | 106.65 | 60.38 |
| 1.69 | 104.54 | 58.93 |
| 1.82 | 100.87 | 57.47 |
| 1.95 | 96.48 | 56 |
| 2.07 | 92.46 | 54.45 |
| 2.2 | 89.1 | 52.81 |
| 2.34 | 86.21 | 51.15 |
| 2.47 | 83.57 | 49.55 |
| 2.59 | 81.09 | 48.04 |
| 2.73 | 78.65 | 46.51 |
| 2.85 | 76.5 | 45.11 |
| 2.98 | 74.49 | 43.79 |
| 3.11 | 72.56 | 42.51 |
| 3.23 | 70.72 | 41.29 |
| 3.37 | 68.93 | 40.1 |
| 3.49 | 67.25 | 38.97 |
| 3.63 | 65.63 | 37.87 |
| 3.75 | 64.17 | 36.87 |
| 3.88 | 62.78 | 35.93 |
| 4.01 | 61.45 | 35.01 |
| 4.14 | 60.21 | 34.16 |
| 4.27 | 58.99 | 33.32 |
| 4.4 | 57.83 | 32.52 |
| 4.52 | 56.75 | 31.78 |
| 4.65 | 55.75 | 31.1 |
| 4.78 | 54.79 | 30.44 |
| 4.9 | 53.85 | 29.79 |
| 5 | 53.18 | 29.34 |

FIG. 15

INPUT PARAMETERS

| PATIENT | AGE |  |
|---|---|---|
|  | GENDER |  |
|  | HEIGHT |  |
|  | WEIGHT |  |
|  | CARDIAC OUTPUT (GOOD, FAIR, POOR) |  |
| INJECTION | UNI- vs. BIPHASIC | UNI |
|  | VOLUME | 120ml |
|  | CONCENTRATION | 300 mgI/ml |
|  | INJECTION RATE | 3ml/sec |
| CT SCAN | EXAM TYPE (LIVER, VASCULAR) | LIVER |
|  | SCAN DURATION | 30 seconds |

OUTPUT PARAMETERS:

PREDICTED CONTRAST ENHANCEMENT CURVE
ENHANCEMENT ADEQUACY (y/n)
       SCAN DURATION ABOVE ADEQUACY THRESHOLD
       IF NO, INCREASE VOLUME, OR RATE
       IF YES, DECREASE VOLUME, OR RATE
OPTIMAL SCAN DELAY
              CARDIAC OUTPUT = 100%

| TIME | PREDICTED HEPATIC ENHANCEMENT LEVEL | SUBTRACT THRESHOLD OF ADEQUACY (50 HU) | COMPUTE AREA UNDER CURVE (AUC) OVER SCAN DURATION (30 SECONDS) | OPTIMAL TEMPORAL WINDOW |
|---|---|---|---|---|
| SECONDS | HU | HU | HU•SEC |  |
| 0 | 0 | -50 |  |  |
| 5 | 0 | -50 |  |  |
| 10 | 0 | -50 |  |  |
| 15 | 1 | -49 |  |  |
| 20 | 4 | -46 |  |  |
| 25 | 10 | -40 |  |  |
| 30 | 17 | -33 |  |  |
| 35 | 25 | -25 |  |  |
| 40 | 34 | -16 | 9.6 |  |
| 45 | 43 | -7 | 129.0 |  |
| 50 | 49 | -1 | 205.6 |  |
| 55 | 53 | 3 | 246.6 |  |
| 60 | 56 | 6 | 263.8 |  |
| 65 | 58 | 8 | 263.7 | START SCAN |
| 70 | 58 | 8 | 252.6 |  |
| 75 | 58 | 8 | 233.9 |  |
| 80 | 58 | 8 | 209.8 |  |
| 85 | 58 | 8 | 181.9 |  |
| 90 | 57 | 7 | 151.4 | END SCAN |
| 95 | 56 | 6 | 119.4 |  |
| 100 | 55 | 5 | 86.0 |  |
| 105 | 54 | 4 | 51.5 |  |

SCAN IS STARTED AT MAXIMUM AUC (263.8 HU•SEC) OVER THE SCAN DURATION
(BOLD = SCAN DURATION)

FIG. 20

ADJUST OPTIMAL SCAN TIMING WITH CARDIAC VARIATION

| TIME | CARDIAC OUTPUT=200% | | CARDIAC OUTPUT=100% | | CARDIAC OUTPUT= 75% | | CARDIAC OUTPUT= 50% | | ACTUAL AORTIC ENHANCEMENT LEVEL | ACTUAL AORTIC ENHANCEMENT AUC |
|---|---|---|---|---|---|---|---|---|---|---|
| | PREDICTED AORTIC ENHANCEMENT LEVEL | PREDICTED AORTIC ENHANCEMENT AUC | PREDICTED AORTIC ENHANCEMENT LEVEL | PREDICTED AORTIC ENHANCEMENT AUC | PREDICTED AORTIC ENHANCEMENT LEVEL | PREDICTED AORTIC ENHANCEMENT AUC | PREDICTED AORTIC ENHANCEMENT LEVEL | PREDICTED AORTIC ENHANCEMENT AUC | | |
| SECONDS | HU | HU•SEC | HU | HU•SEC | HU | HU•SEC | HU | HU•SEC | HU | HU•SEC |
| 0 | 0 | 0 | 0 | 0 | 0 | 0 | 0 | 0 | 0 | 0 |
| 5 | 11 | 56 | 0 | 1 | 0 | 0 | 0 | 0 | 0 | 0 |
| 10 | 60 | 354 | 22 | 113 | 7 | 37 | 0 | 2 | 8 | 39 |
| 15 | 93 | 819 | 72 | 475 | 48 | 275 | 11 | 56 | 47 | 273 |
| 20 | 115 | 1391 | 120 | 1074 | 99 | 768 | 45 | 281 | 101 | 776 |
| 25 | 134 | 2059 | 158 | 1864 | 148 | 1508 | 95 | 755 | 150 | 1527 |
| 30 | 152 | 2819 | 187 | 2801 | 190 | 2459 | 151 | 1509 | 192 | 2485 |
| 35 | 169 | 3663 | 212 | 3864 | 225 | 3582 | 200 | 2507 | 223 | 3601 |
| 40 | 147 | 4396 | 220 | 4965 | 249 | 4828 | 242 | 3716 | 248 | 4841 |
| 45 | 121 | 5003 | 189 | 5912 | 244 | 6047 | 279 | 5109 | 242 | 6050 |
| 50 | 110 | 5553 | 159 | 6705 | 210 | 7097 | 287 | 6544 | 212 | 7109 |
| 55 | 104 | 6074 | 140 | 7403 | 179 | 7990 | 269 | 7890 | 180 | 8007 |
| 60 | 98 | 6565 | 127 | 8039 | 157 | 8774 | 240 | 9092 | 157 | 8794 |
| 65 | 93 | 7031 | 120 | 8640 | 142 | 9483 | 206 | 10124 | 142 | 9504 |
| 70 | 89 | 7476 | 116 | 9220 | 132 | 10142 | 185 | 11047 | 131 | 10159 |
| 75 | 85 | 7902 | 112 | 9781 | 126 | 10770 | 165 | 11872 | 125 | 10785 |
| 80 | 81 | 8309 | 109 | 10324 | 122 | 11379 | 151 | 12629 | 121 | 11392 |
| 85 | 78 | 8696 | 105 | 10850 | 119 | 00975 | 140 | 13329 | 118 | 11984 |
| 90 | 74 | 9068 | 102 | 11362 | 116 | 12556 | 133 | 13992 | 115 | 12560 |
| 95 | 72 | 9426 | 100 | 11862 | 113 | 13122 | 128 | 14630 | 112 | 13119 |
| 100 | 69 | 9771 | 98 | 12352 | 110 | 13671 | 124 | 15252 | 109 | 13662 |
| 105 | 67 | 10104 | 96 | 12831 | 106 | 14202 | 123 | 15866 | 106 | 14190 |
| 110 | 64 | 10426 | 94 | 13299 | 104 | 14721 | 122 | 16474 | 103 | 14705 |
| 115 | 62 | 10738 | 91 | 13754 | 102 | 15231 | 120 | 17074 | 101 | 15211 |
| 120 | 60 | 11040 | 89 | 14197 | 100 | 15733 | 118 | 17665 | 100 | 15709 |
| 125 | 59 | 11333 | 86 | 14629 | 99 | 16228 | 116 | 18244 | 98 | 16200 |
| 130 | 57 | 11617 | 84 | 15050 | 98 | 16716 | 113 | 18810 | 97 | 16685 |
| 135 | 55 | 11894 | 82 | 15460 | 96 | 17197 | 111 | 19364 | 95 | 17160 |

ACTUAL AORTIC ENHANCEMENT AUC IS 776 HU•SEC AT 20 SECONDS (BOLD) AND MOST CLOSELY MATCHES PREDICTED AORTIC ENHANCEMENT AUC AT 20 SECONDS (768 HU•SEC) FOR PATIENT WITH CARDIAC OUTPUT OF 75%. OPTIMAL TEMPORAL WINDOW FOR HEPATIC ENHANCEMENT IS COMPUTED BY ANALYZING PREDICTED HEPATIC ENHANCEMENT CURVE FOR PATIENT WITH CARDIAC OUTPUT OF 75% (FIG.25).

FIG. 24

CALCULATION OF THE TEMPORAL WINDOW FOR OPTIMAL ENHANCEMENT

CARDIAC OUTPUT = 75%

| TIME | PREDICTED HEPATIC ENHANCEMENT LEVEL | SUBTRACT THRESHOLD OF ADEQUACY (50 HU) | COMPUTE AREA UNDER CURVE (AUC) OVER SCAN DURATION (30 SECONDS) | OPTIMAL TEMPORAL WINDOW |
|---|---|---|---|---|
| SECONDS | HU | HU | HU ∘ SEC | |
| 0 | 0 | -50.0 | | |
| 5 | 0 | -50.0 | | |
| 10 | 0 | -50.0 | | |
| 15 | 0 | -49.7 | | |
| 20 | 2 | -48.5 | | |
| 25 | 4 | -45.6 | | |
| 30 | 9 | -40.7 | | |
| 35 | 16 | -34.3 | | |
| 40 | 23 | -27.4 | | |
| 45 | 30 | -19.8 | | |
| 50 | 38 | -11.6 | 23.8 | |
| 55 | 45 | -5.2 | 122.8 | |
| 60 | 49 | -0.5 | 191.0 | |
| 65 | 53 | 2.8 | 236.3 | |
| 70 | 55 | 5.1 | 264.5 | |
| 75 | 57 | 6.6 | 279.2 | |
| 80 | 58 | 7.6 | 284.0 | START SCAN |
| 85 | 58 | 8.2 | 281.3 | |
| 90 | 58 | 8.5 | 272.6 | |
| 95 | 59 | 8.5 | 259.3 | |
| 100 | 58 | 8.4 | 242.1 | |
| 105 | 58 | 8.0 | 222.3 | |
| 110 | 58 | 7.6 | 200.7 | END SCAN |
| 115 | 57 | 7.1 | 177.8 | |
| 120 | 56 | 6.4 | 154.2 | |
| 125 | 56 | 5.8 | 130.1 | |
| 130 | 55 | 5.1 | 105.7 | |
| 135 | 54 | 4.4 | 80.6 | |
| 140 | 54 | 3.7 | 54.8 | |
| 145 | 53 | 3.0 | | |
| 150 | 52 | 2.3 | | |
| 155 | 52 | 1.6 | | |
| 160 | 51 | 0.9 | | |
| 165 | 50 | 0.1 | | |
| 170 | 49 | -0.7 | | |

SCAN IS STARTED AT MAXIMUM AUC (284.0 HU∘SEC) OVER THE SCAN DURATION
(BOLD = SCAN DURATION)

FIG. 25

METHOD OF AND APPARATUS FOR PREDICTING COMPUTED TOMOGRAPHY CONTRAST ENHANCEMENT WITH FEEDBACK

CROSS-REFERENCE TO RELATED APPLICATION

This application is a continuation-in-part of application Ser. No. 08/539,859, filed Oct. 6, 1995, now U.S. Pat. No. 5,583,902, the disclosure of which is incorporated herein by reference.

FIELD OF THE INVENTION

This invention relates generally to an apparatus and method for predicting organ specific contrast enhancement prior to computed tomography scanning of a patient. Specifically, this invention relates to a computer simulation of contrast agent transport throughout the body to predict organ specific enhancement in patients of variable height and weight subjected to various contrast injection protocols to enable operator selection of an appropriate injection protocol prior to commencing the scan and to use measurements of actual contrast agent transport throughout the body after injection as feedback to verify and calibrate the predictions.

BACKGROUND OF THE INVENTION

Computed tomography (CT) is a widespread diagnostic imaging method which measures the x-ray attenuation coefficient of matter. This x-ray attenuation coefficient is depicted in terms of Hounsefield Units (HU). During a CT scan, a collimated X-ray beam is directed on the patient and the attenuated remnant radiation is measured by a detector whose response is transmitted to a computer. The computer considers the location of the patient and the spatial relationship of the x-ray beam to the region of interest. The computer analyzes the signal from the detector so that a visual image can be reconstructed and displayed on a monitor. The image can then be viewed or stored for later evaluation.

Hounsefield Units reflect the relative absorption of CT x-rays by matter, the absorption being related to the atomic number, electron density, physical thickness of that matter, and the energy spectrum of the x-rays. Because of the similarity in electron density of various tissues in the body, CT scans sometimes result in poor imaging. In an attempt to obtain better results in such circumstances, a contrast agent, such as iodine, can be injected in the parent's blood stream to change the relative radio-density of the tissues, and improve overall diagnostic efficacy.

When using a contrast agent, it is extremely important to coordinate the time of the scan with the time of greatest levels of contrast in the region of interest, in some instances with respect to a threshold value. Because the contrast agent is injected into the blood stream, many physiological factors can affect the start time and duration of a sufficient level of contrast in the region of interest. For example, because the cardiovascular system provides the means for circulation of contrast agent throughout the body after it is injected into the blood stream, a patient's cardiac output can have a significant effect on the distribution of the contrast agent as well as the time taken for the contrast agent to reach a particular organ or vessel.

Current understanding of intravenous contrast enhancement is further complicated by multiple interacting factors including contrast agent type, volume and concentration, injection technique, catheter size and site, scanning technique, patient characteristics and tissue characteristics. Of these factors, all of which have influence on contrast enhancement, the variables which cannot be controlled are those related to the patient. These include age, gender, weight, height, cardiovascular status, renal function and other disease status. In the past ten years, many clinical studies testing various intravascular contrast agent and injection protocols have been reported. However, in many respects, contrast enhancement still relies heavily on the experience and intuition of the physician rather than rigorous, quantitative analysis of the mechanism of contrast enhancement.

SUMMARY OF THE INVENTION

The invention of the parent provides a method of and an apparatus for predicting tissue specific CT contrast enhancement in a patient with a specific body habitus subjected to different contrast injection protocols. The method is preferably implemented in a computer program, and the computer itself may be used to also control the CT scan in accordance with an operator's choice. Such a physiological model of contrast enhancement has many potential clinical applications.

The invention of the parent utilizes a compartmental model of the human cardiovascular system and assigns differential equations describing mass transport to each compartment of the model. Regional circulation parameters such as blood volume, regional blood flow and extracellular fluid volume were estimated using available data to provide input to the equations. Local tissue structures such as organs and vessels were modeled mathematically to describe the distribution and dispersion of an intravascularly-administrated contrast agent. A global model was then formed by integrating the regional circulation parameters with the models of local tissue structures.

The invention of the parent allows an accurate prediction of the time varying distribution and concentration of contrast in the body. This in turn allows an operator to predict the time and duration of maximum enhancement in a specific organ or tissue in a patient for a particular injection protocol. Most importantly, the operator can use the invention of the parent to predict the time a scan should be started and the duration of the scan based on output data from the program. This output can take the form of a data stream or can be a graph of contrast enhancement, versus time. With more advanced generations of CT machines, such as spiral and helical CT scanners as are known in the art, a typical scanning procedure can be completed within approximately 30 seconds. The invention of the parent enables an operator to choose an injection protocol to ensure that the entire scan takes place during a period of maximum enhancement, and while enhancement exceeds a suitable threshold.

In the prior art, there are devices which monitor and output contrast enhancement levels for a region of interest. Using these prior art devices, an operator injects the contrast agent into the patient, views the output, and determines when to begin a scan based on when the enhancement level attained in the patient's region of interest becomes acceptable. The prior art devices require the injection of the contrast agent and low dose x-rays of the region of interest. For example, in the prior art, the injection of a contrast agent is started and the prior art device monitors at regular intervals the enhancement level in the region of interest and provides an output. The operator can view the output and then decide when to begin the scan.

As explained in the parent, prior art techniques to determine the enhancement level in an organ include low dose pre-scanning of the organ during injection of the contrast. One such example is U.S. Pat. No. 5,459,769 to Brown. In Brown, after a short delay upon initiating the injection, low-dose x-rays are taken of the organ to be scanned. Images are constructed from the low-dose x-rays and the images are displayed for the operator to determine when the enhancement level in the organ is sufficient to begin a full dose scan.

The invention of the parent is a significant improvement over the prior art in that it allows prediction of contrast enhancement levels and duration of those enhancement levels prior to injection of the contrast agent and without the need of low dose x-rays. Moreover, because different injection variables, such as rate and concentration, can alter the enhancement levels, the invention of the parent allows calculation of various alternatives to choose the best injection scheme for a particular patient. The prior art devices do not assist the operator in determining whether a particular patient having a specific body habitus will even acquire a desired threshold level of enhancement with a given injection protocol.

Therefore, if the threshold level of enhancement is never reached because of the patient's specific body habitus or an improper injection protocol for the particular patient, a scan cannot be completed and the entire process must be repeated, including a second injection. Even then, the operator cannot be certain that the revised injection will ever reach a desired threshold level of enhancement based on that patient's specific body habitus and injection protocol, nor whether the threshold level, if attained, will be maintained during the entirety of a desired scan duration. This is particularly important for scans of certain tissues whose contrast enhancement behavior is complex, as explained in greater detail below.

The invention of the parent also allows an operator to adjust the collimation or slice thickness and CT table speed to optimize a scan. During a CT scan, a patient lies on a table which moves through the CT scanner from head to toe vertically, and over the selected region of interest. The collimation or slice thickness is the thickness of the slice of the patient's body that is transaxially scanned. The table can usually be moved at a rate per second of up to two times the collimation thickness. Using the method and apparatus of the parent, an operator can optimize the collimation rate and table speed. For example, if there is a limited period of threshold enhancement, the operator knows that an increased table speed or an increased collimation thickness must be used to ensure that the entire scan is completed during the time period of maximum enhancement. Customizing the scan is less precise with the prior art.

In the invention of the parent, the computer program allowed an operator to determine how long the predicted enhancement level exceeded the threshold enhancement. That information provided the operator with a means to adjust various scan parameters such as scan duration, scan start time and table speed, to be certain that the scan took place during a period when the predicted enhancement was above a threshold enhancement. Thus, the invention was a significant improvement over the prior art.

Building on the invention disclosed in the parent, the inventors herein have improved it by providing for a method of using the predicted enhancement levels to optimize injection protocol and adjust the injection parameters to increase or decrease the time that the predicted enhancement level exceeds the threshold. The inventors have also improved it by providing a means for determining the optimum scan start time when the predicted enhancement level exceeds the threshold for a period much greater than the scan duration.

The present invention can be implemented in many ways including a separate computer or integrated with the computer of a CT machine. All that is required is a computer having the invention programmed therein integrated with the controls of the machine. The present invention can also be implemented in a contrast injector system which is equipped with a computer for predicting contrast enhancement for given inputs of patient parameters and contrast injection protocol. In this way, adjustments to the injection protocol are readily made using the injector.

The contrast injector having a computer with the invention programmed therein can be operated as a fully integrated system with a CT scanner or as an independent system. When the present invention is used as a part of a computer system integrated with both an injector system and a CT scanner equipped with low-dose pre-scan CT, the optimal set of scan parameters can be adjusted based on actual enhancement measurements acquired with low-dose scanning.

The invention of the parent is capable of using standard values for variables which influence enhancement levels and also allow input of patient specific values. For example, a particular patient habitus may be such that the standard values for variables such as blood volume, blood flow etc., will not provide an accurate prediction of enhancement levels. The invention of the parent utilizes several methods to resolve such situations. One method provides for the input of patient specific information to customize the operation to the particular patient. This includes patient specific variables such as weight, age, height and gender. These variables can be measured and input to adjust the standard variables accordingly.

On occasion, other variables which are not readily measurable may need to be modified. As is well known in the art, cardiac output cannot be measured as readily as height or weight. Of course, a patient with a known history of heart failure or increased age will most certainly have a cardiac output below normal. If this is the case, the invention of the parent allows adjustment of the standard variables accordingly.

Another aspect of the method in the parent allows the operator to choose several alternative values for cardiac output and generate a family of predicted enhancement curves for each value. After injection of contrast agent is started, actual measurements of enhancement can be compared to the initial portions of the family of curves to determine which family member most closely resembles the actual results. In this way, early in the scan and before the threshold has been reached, a choice of which curve to utilize to best predict when the scan should occur can be made. This choice can be made by the operator or automatically by the computer.

The inventors herein have improved upon the method of the parent by using predicted aortic enhancement levels compared with sequential measurement of actual aortic enhancement levels using low-dose pre-scanning as an indicator of unknown patient specific parameters such as the cardiac output of the patient.

In the present invention, the predicted enhancement levels are computed for a given set of patient specific parameters in an injection protocol. Prior to any injection of the contrast into the patient, the operator enters the patient specific parameters and the injection protocol into the computer which can be integral with an injector, a CT scanner or be a stand-alone personal computer. The method of the present invention provides an output from the computer which gives the predicted tissue enhancement level of the tissue to be scanned as a function of time. Based on that output, the operator uses the present invention to modify the injection protocol in order to ensure that the predicted tissue enhancement function exceeds a threshold level for at least as long as the desired scan duration.

If the predicted tissue enhancement function is shown by the output to be substantially greater than the threshold level, the present invention allows the operator to modify the injection protocol to decrease the volume or flow rate. If the predicted enhancement function does not meet or exceed the threshold level or does not exceed the threshold level for the length of the scan duration, the present invention allows modification of the injection protocol by increasing the flow rate or volume of contrast. The program iterates to again compute and provide a revised predicted tissue enhancement function output based on the revised injection and/or rate.

If the predicted tissue enhancement function is known to be above the threshold level for a period of time substantially greater than the desired scan duration, the operator can use the method above to decrease the injection rate or volume of contrast or both to reduce the predicted enhancement level to a range which still satisfies the scan parameters, thereby saving contrast agent and minimizing any potential side effects to the patient. In the alternative the method provides for prediction of the optimal temporal window for performing the scan within the period that the enhancement exceeds the threshold.

After the operator is satisfied that the injection protocol chosen and the patient specific parameters will produce an acceptable enhancement level as shown by the output of the present invention, the operator can further increase the accuracy of the prediction by predicting and low-dose monitoring enhancement in a region of interest and comparing the prediction with the actual measurement from the monitoring to update or revise the predicted tissue enhancement function. In this way, the invention uses feedback from actual enhancement measurements to fine tune the predictions.

To practice this aspect of the invention, the operator performs a base line scan over a distinct region of interest. The base line scan is a low-dose or partial scan in which the x-ray dosage is reduced substantially less than a typical scan. After completing the base line scan, the operator begins the injection of the contrast agent. After initiating the injection, the operator performs low-dose pre-scan of the region of interest, such as the aorta, to obtain actual aortic enhancement levels. The pre-scan is virtually identical to the base line scan described above and is also a low-dose scan and can use less than a full revolution of the gantry of a CT scanner. Using the actual measurement of enhancement in the aorta, the present invention can calibrate the model for patient parameters such as cardiac output and provide revised tissue enhancement predictions.

The present invention has particular application where the organ or vessel being scanned is incapable of maintaining threshold enhancement levels for a sustained period. One such example is CT angiography. In CT angiography, a CT scan is taken of a blood vessel or vessels. Unlike organs, blood vessels do not maintain high enhancement levels over time and the timing of the scan is critical. CT angiography is performed in the prior art by injecting a test dose of contrast agent and measuring with low dose x-rays the elapsed time for the contrast agent to reach the region of interest. Thereafter, a full dose of contrast agent is injected and a scan is initiated after lapse of the previously measured time delay. However, there is no guarantee of a particular enhancement level being attained or sustained as required to achieve a successful scan. Using the invention comprising the method and apparatus disclosed herein, one can more accurately predict not only the time delay, but also the degree of enhancement and its duration.

While the principal advantages and features of the invention have been described above, a greater understanding of the invention may be attained by referring to the drawings and the description of the preferred embodiment which follow.

BRIEF DESCRIPTION OF THE DRAWINGS

FIG. 15 is a data stream output generated by the invention of the parent showing predicted aortic and hepatic enhancement levels in a hypothetical patient with standard blood volume and standard cardiac output using uniphasic-high flow rate injection protocol in Table Six;

FIG. 20 is a table showing an output of the present invention using the process steps in the flow chart of FIG. 21;

FIG. 24 is a table generated using the present invention showing four predicted aortic enhancement levels for four alternative cardiac outputs and the actual predicted enhancement levels at specified elapsed times after injection with the corresponding area under the enhancement curve (AUC) calculations;

FIG. 25 is a table generated using the present invention showing predicted hepatic enhancement levels at specified elapsed times after injection using the cardiac output calculated from the table of FIG. 24.

DETAILED DESCRIPTION OF THE PREFERRED EMBODIMENT

Figure 1:
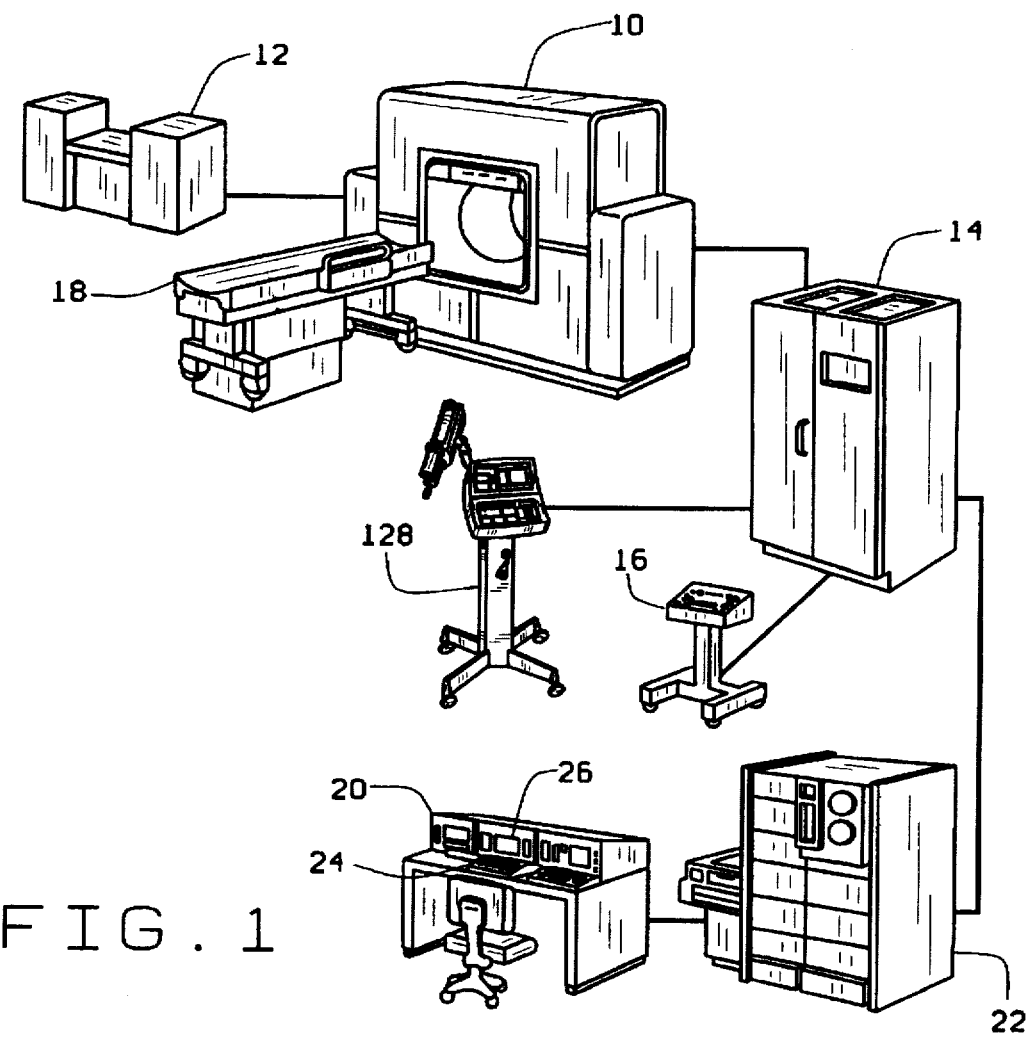
FIG. 1 is a diagram showing the components of a complete CT scanner system and a computer control console.

Computed Tomographic (CT) scanning is an invaluable radiologic diagnostic tool. The major components of a conventional CT scanner are shown in FIG. 1. The CT scanner 10 contains the x-ray tube and detector array. Power is supplied by a high voltage generator 12 controlled by scanner electronics 14 and scanner service module 16. The patient support and positioning couch 18 is moveable to transport the patient through the scanner 10. The scanner 10 and voltage generator 12 receive electronic commands from the operating console 20 and transmit data to the computer system 22 for image production and analysis. The operating console 20 usually contains an interactive keyboard 24 and CRT monitor 26.

Many radiographic procedures, including CT scans, require an injection of contrast medium under specific control conditions. For example, CT scanning requires a high degree of control over the injection of the contrast agent and the parameters of the injection protocol in order to maximize the accuracy of the scan. It would be difficult to consistently perform these injections by hand. Therefore, these injections are usually performed with a mechanical-type device known in the art as power injectors or injector systems. Injector systems allow significant control of the injection of contrast into a patient prior to a CT scan.

Figure 17:
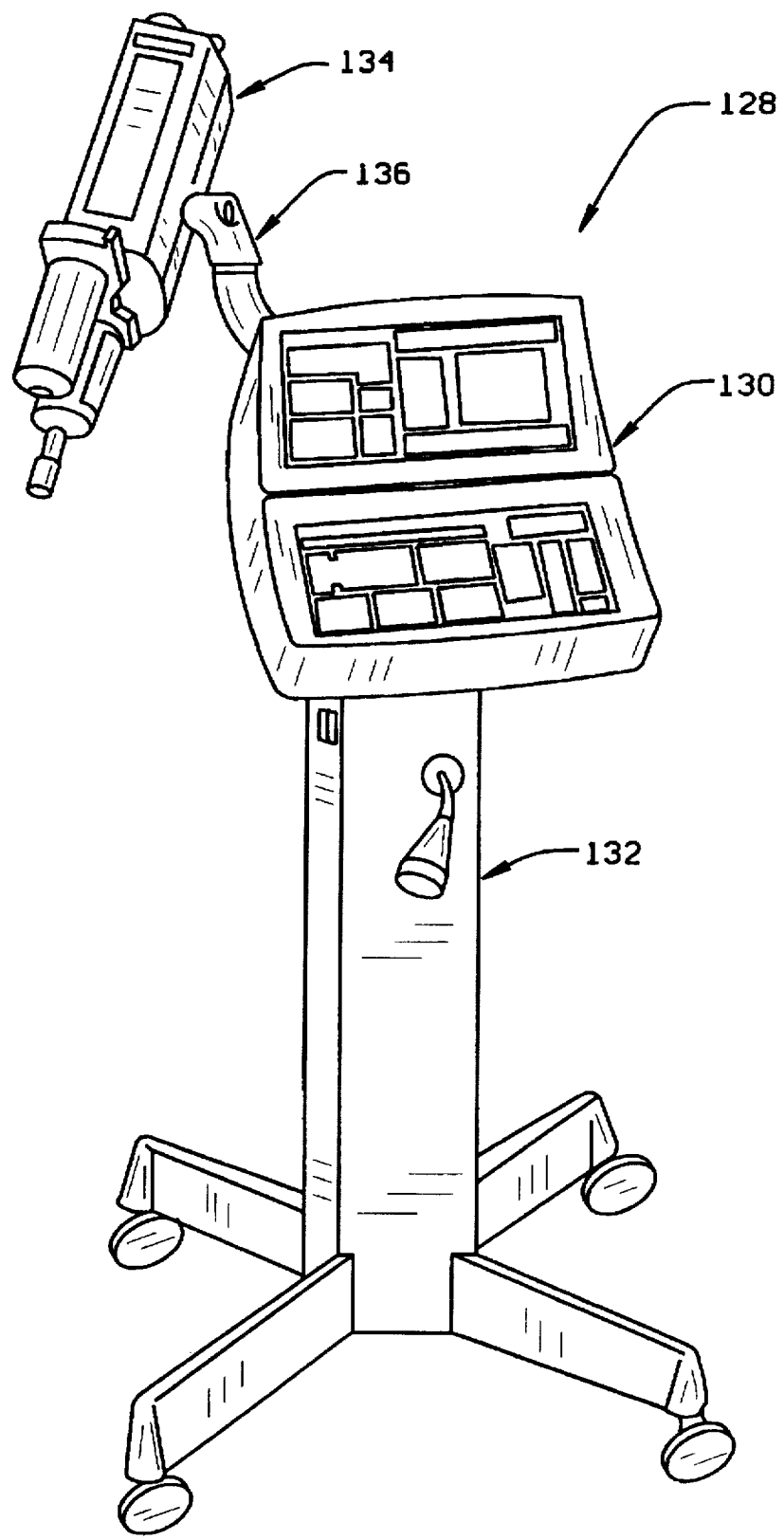
FIG. 17 is a drawing of a power injector system with its various components.

Injection systems for CT scans have several basic components. An example of an injector system is shown generally as 128 in FIG. 17. The injector system includes a control unit 130, mounted on a pedestal 132, an injector head 134 and arm 136 integral to the unit. The entire injector system 128 can be wheeled about as a unit for use with the CT scan machine as shown in FIG. 1. The control unit of the injector comprises a control panel for setting up the injection and a display for displaying instructions and data. The controls and indicators present on the control panel will vary with the type of options available on the system. One example of an injector system is the Mark V Plus injection system manufactured by Medrad of Pittsburgh, Pa.

The injector head accommodates a syringe and provides for power injecting. The arm connects the head to the console permitting easy movement for loading or injecting. The height allows placement of the head over the patient during a CT scan. In the alternative, the injector head and arm can be mounted to the CT scan table, or overhead from a ceiling mount, or wall mounted near a CT system with the control panel being located on a console integrated with the controls of the CT scan.

The injector head can be either floor mounted or track mounted on an overhead system. In most cases, the control panel is mounted inside the CT scan control booth for operator safety. Most injector systems also contain a microprocessor and memory for storing computer programs which can be recalled when needed. A warming system may also be included in an injector system which warms and maintains the contrast medium at or near body temperature. This will help reduce viscosity of contrast medium, resulting in a decrease in resistance of contrast medium flow and decrease in a patient discomfort experienced during injection. Most injector systems use a power high pressure mechanism, such as an electric drive motor coupled to a jack screw, to drive the piston in or out of the syringe and deliver the contrast.

Injector systems can also be interfaced with a CT imaging system. This interfacing of an injector to a CT imaging system allows variations such as causing the injector to be triggered by the imaging system or causing the imaging system to be triggered by the injector. Bi-directional controls are also available to allow either device to control the other and allow an operator to choose how to sequence and time the devices when they are connected. For example, the CT scan imaging system can have a control which allows it to trigger the injector and the injector can have a control which allows the injector to send a signal to the CT imaging system to trigger the start of a scan. The details of interfacing the injector system with an imaging system and the controls available are well-known in the art.

The control panel on an injector system is used to set the parameters of the injection sequence. It usually consists of an alpha-numeric keyboard and buttons for various input parameters as well as several display windows including a window for displaying system messages. The control panel accepts and displays injection parameters, displays injection results and other messages related to the control of the injector system. The control panel allows the operator to program the injector system to control various parameters of the injection process including the flow rate, volume, injection duration, injection pressure, and injection delay. The flow rate is defined as the delivery rate of the contrast (amount delivered per unit of time). The flow rate is dependent on the viscosity of the contrast agent, the length and diameter of the catheter, and the injection pressure. The particular flow rate chosen for a specific procedure is governed by the procedure itself, the vessel entered and the patient habitus. Flow rates can vary from as low as 0.1 ml/s to as high as 40 ml/s, depending on these factors.

The present invention is preferably implemented in a computer program. Because most CT scanners and injector systems utilize computers to control their operation, the present invention could be easily integrated therewith. In that fashion, the operator could run the program prior to the injection or prior to the scan and the computer can determine the optimum injection and scan parameters and using the determined values complete the injection and the scan accordingly. In this way, the injection system computer or the CT scan computer (or the shared computer on a combined system) can determine as well as implement the injection protocol and the scan parameters. In the alternative, a separate computer which contains the program could be utilized. The scan parameters and injection protocol could be determined by running the program in the separate computer and then input into the injector system computer or CT scan computer by the operator or through computer data transfer methods.

Figure 2:
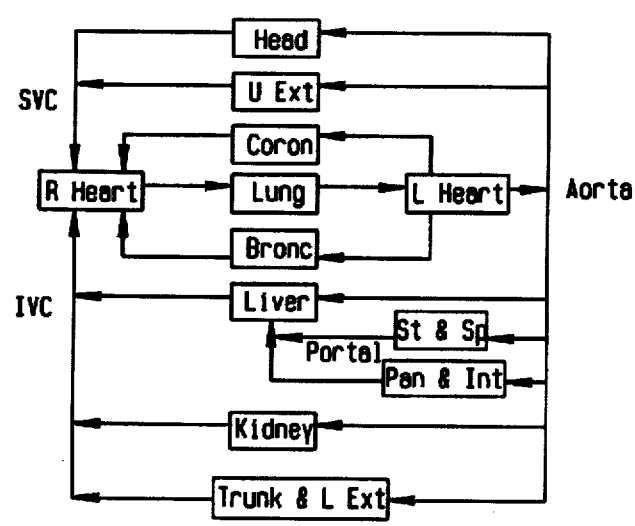
FIG. 2 is a schematic diagram of the major organs of a human cardiovascular circulation system.

The invention of the parent utilizes a model of the human cardiovascular system to describe mass transport of contrast agent throughout the body. The cardiovascular system provides the means for circulation of contrast agent throughout the body after it is injected into the bloodstream. The human cardiovascular system is very complex and has numerous controlling mechanisms, including neuronal, hormonal and psychological controls. A simplified human cardiovascular system as shown schematically in FIG. 2 consists of the heart, vascular networks, and key organs which serve as reservoirs. Normal blood volume and flow distribution throughout the body are well established in the prior art and are given in the Tables 1 and 2 (All Tables are shown in Exhibit A attached hereto and incorporated herein by reference).

Based on well known information, the model of the parent assumed that the average blood volume was 5 liters. This includes 3 liters of plasma and 2 liters of red blood cells. The average cardiac output was also estimated from known sources to be 6.5 liters per minute. These values were used to describe a standard model of the cardiovascular system. However, the method and apparatus of the parent allow these values to be adjusted according to the patient's age, gender, weight and height using standard nomograms outlined below.

Because contrast agent diffuses passively from the bloodstream across the capillary membrane into the extravascular space, the distribution of fluid throughout the body was included in the cardiovascular model. The amount of total body water (TBW) in an adult of average weight (70 Kg) was assumed to be 40 L. TBW was divided into two major components, intracellular fluid (ICF) and extracellular fluid (ECF). The ECF was further divided into several smaller compartments including interstitial fluid, plasma, and cerebrospinal fluid. The interstitial fluid is the largest compartment and lies in the lymphatics and the spaces between cells.

The ECF volume is usually estimated with dilution methods in which a substance is injected into the blood stream and diffuses throughout the entire extracellular fluid compartment with little entering into the cells. However, an ideal substance for such dilution studies has not been identified, and measurements for a 70 kg adult have ranged from 9 L to 22 L depending on the substances used. The size of the measured ECF decreases with increases in the molecular weight of the substance used. The apparent volume distribution of iohexol has been reported to be 0.27 l/kg. Thus, for a 70 Kg adult, this equates to an ECF of 18.9 L. In the model of the parent this value for ECF volume was used which includes a plasma volume of 3.0 L. The overall estimated distribution of body fluid used in the cardiovascular model is summarized in Table 3.

The detailed distribution of fluid in a local organ was estimated from the standard mass of an organ and its water content. The volume of the total systemic capillary bed is estimated to be about 300 ml. However, a detailed breakdown of capillary volumes in different regions is not available. In addition, the number of capillaries within an organ varies considerably from one organ to another. It is believed that the regional capillary volume is directly proportional to a regional blood flow and the cardiovascular model of the parent applied this assumption. These values are likely overestimated in highly perfused organs such as the kidney and the liver but this did not hinder the performance of the model. Table 4 shows the regional capillary volumes in the systemic circulation estimated from the regional blood flow values given in Table 2.

A calculation of the regional distribution of the extracellular and intracellular fluid was also necessary for the invention of the parent. The regional distribution of total body fluid can be calculated from the known mass of each organ and its water content, assuming a density of 1.0 g/Ml. The weight and percent of water content of the visceral organs are shown in Table 5 along with their total fluid value minus the capillary volume. Without available information, the model of the parent assumes 70% water content in the stomach, spleen and intestine. The lung consists of 50% parenchyma and 50% non-parenchyma tissues whose capillary volumes are 150 ml and 5 ml, respectively.

The total body fluid of the upper extremities, trunk, and lower extremities was calculated by subtracting from the total body water volume (40 L), the blood volume (5 L), and the total fluid of the visceral organs minus the capillaries (4,726 mL). The mass ratio of the lower extremities and trunk to the upper extremities is about 4:1. Thus, the total body fluid of the upper extremities becomes 6,055 mL and that of the lower extremities and trunk, 24,219 mL.

Table 3 shows the overall volumes of ICF fluid and ECF fluid as 19.1 L and 15.9 L. respectively. However, regional distribution of the ICF and ECF is not shown. Some tissues such as the skin, adipose tissue, G-I tract, and liver have larger extracellular to intracellular fluid ratios than, for example, muscle. As no data regarding such fluid ratios are available, in the parent, it was assumed the ratio of ECF to ICF to be the same in all body regions. For example, the ECF and ICF volumes of the liver were estimated as 524 and 629 mL respectively.

After regional blood flow, blood volume, and distribution of body fluid were estimated, local structures were modeled mathematically to describe the distribution and dispersion of intravascularly administered iodinated contrast agent within local regions. The blood vessels are viscoelastic with complex mechanical properties to accommodate pulsatile blood flow and various pressure gradients. Although the blood flow in large vessels is generally streamlined, some mixing occurs within the blood vessel because of molecular diffusion, flow pulsability and convections at multiple branching points. The dispersion may be even greater in smaller and low pressure vessels. To simplify the model of the parent, blood vessels were represented as rigid structures without directly incorporating their dynamic pulsatile properties in the.

A blood vessel could be analyzed in the cardiovascular model as a simple conduit without any longitudinal mixing. This is known in the art as "plug flow." In this type of model, each artery and vein is divided into segments, and blood enters as plugs for each heartbeat and displaces an equal volume of blood without any longitudinal mixing. The major problem with this approach is excessive demands on computer memory required to store the history of each segment throughout the circulation. An alternative approach is to consider a blood vessel as a well-stirred compartment or well-mixed pool of blood. This approach simplifies computation, requires far less computer storage and has been shown to perform as well as the plug flow model in the prior art. Thus, in the cardiovascular model of the parent, the heart and blood vessels were analyzed as well-stirred compartments.

Figure 3A:
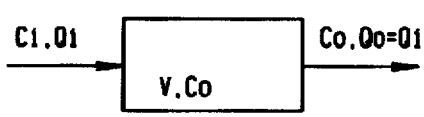
FIG. 3(a) is a block diagram of a single well stirred compartment with an input having a constant input concentration $C_i$ and input flow rate $Q_i$, the compartment having a volume V and an output with a concentration $C_o$ and an output flow rate $Q_o$.

A single, well-stirred compartment contains a constant volume, V, with a single inlet flow and a single outlet flow as shown in FIG. 3(a). $Q_i$ and $Q_o$ represent the input and output volumetric flow rates of the blood, respectively. The input and output flow rates are the same in a constant volume compartment ($Q=Q_i=Q_o$). $C_i$ and $C_o$ represent the input and output concentrations of contrast agent, respectively. Since we assume the compartment to be well mixed, the concentration within the compartment is the same as that of the output. A mass balance of the concentration is described by Fick's Principle, shown schematically in FIGS. 3(a) and 3(b) in the following equation:

$$V*dC_o/dt=Q(C_i-C_o).$$

Figure 3B:
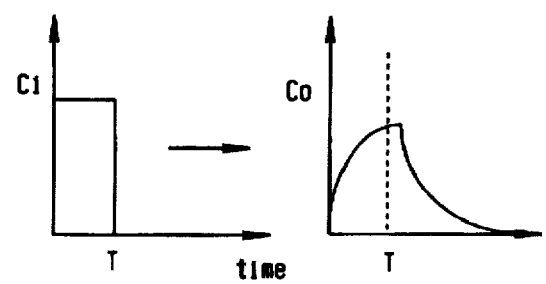
FIG. 3(b) is a graph of the input concentration of the input in FIG. 3(a) and a graph of the corresponding output concentration $C_o$ over time.

For a given volume, V, a given volumetric flow rate Q, and a given input concentration, $C_i$, we can estimate the output concentration, $C_o$, by solving this differential equation. The net effect of a well mixed compartment is to disperse the input concentration over the compartment resulting in more broadly distributed output concentration over time. For constant flow rate, Q over a fixed time interval, T, the input concentration given as a step function is mathematically transformed to the output concentration curve as shown in FIG. 3(b). The transformation is described mathematically as two exponential functions of V, Q and T. The output concentration curve is broader temporally than the input concentration curve, and a central peak is present.

Modeling an organ is more complex than modeling a blood vessel because the contrast agent is no longer confined in the intravascular space and permeates through the capillary membrane into the extravascular space. The simplest approach to modeling an organ is to assume that it also is a well-stirred compartment. However, the single compartment organ model does not address differences in the exchange of contrast agent along subcompartments within an organ and is limited in describing the behavior of substances with different transcapillary permeabilities. A common alternative approach used in the prior art to investigate the distribution of chemotherapeutic agents throughout the body involves splitting each organ into three well known spaces: the capillary or intravascular space (IV), the extracellular space (EC), and the intracellular space (IC). This is shown schematically in FIG. 4(a). For a given organ, each of these three spaces was modeled as a single, well-mixed compartment. Diffusion through membranes, either active or passive, permits exchange of substances along the spaces within the organ. However, because iodinated contrast agent does not penetrate into the cells, only the intravascular (IV) and extracellular (EC) compartments were considered and the intracellular (IC) compartment was ignored.

Figures 4A, 4B:
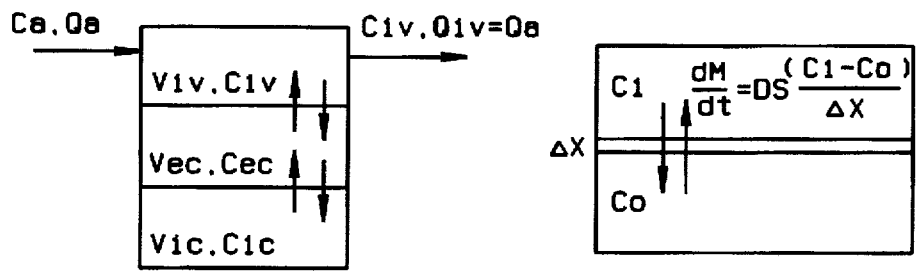
FIG. 4(a) is a block diagram of an organ modeled in three spaces: intravascular (IV), extracellular (EC), and intracellular (IC)
FIG. 4(b) is a block diagram of the IV and EC spaces of FIG. 4(a) detailing the mass transfer rate (dM/dt) therebetween.

Transcapillary exchange of substances between the intravascular and extracellular compartments can be described by Fick's Law of Diffusion and is shown schematically in FIGS. 4(a) and 4(b). The mass transfer rate (dM/dt) is proportional to the diffusion coefficient (D), the surface area (S), and the concentration difference ($C_i-C_o$) for a given membrane thickness (dX) as represented by the following equation:

$$dM/dt=DS(C_i-C_o)/dX.$$

For a thin membrane, the mass transfer rate is simpler such that permeability (P) is commonly used to combine D and dX as a unit resulting in the following equation:

$$dM/dt=PS(C_i-C_o)$$

To complete the mathematical model, two governing differential equations were applied to each organ. One for the intravascular space and the other for the extracellular space. The intravascular space had two transport components. The first component was obtained from blood flow related mass balance, i.e., the inflow of contrast agent minus the outflow. The second component was obtained from the mass balance related to the transcapillary exchange within the extracellular space. For the extracellular space, only one transport component was considered: the mass balance related to transcapillary exchange with the intravascular space. These equations are as follows:

$$V_{iv}*dC_{iv}/dt=q(C_i-C_{iv})-PS(C_{iv}-C_{ec})$$

$$V_{ec}*dC_{ec}/dt=PS(C_{iv}-C_{ec})$$

Figure 5:
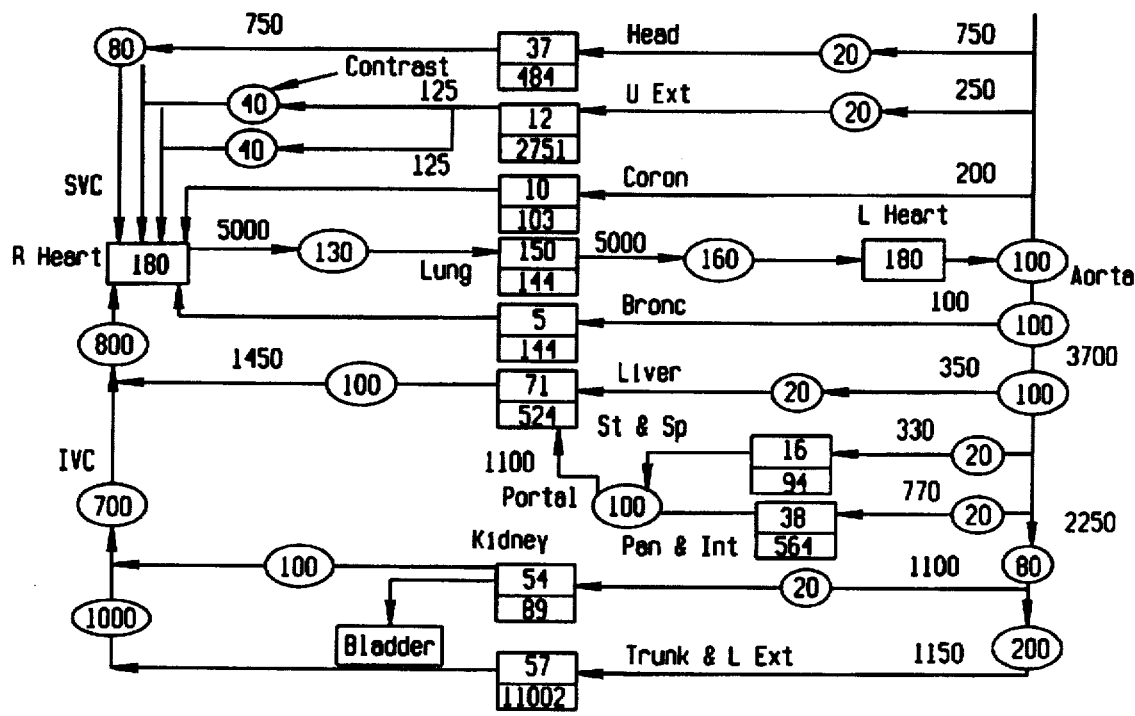
FIG. 5 is a block diagram of the global cardiovascular model of the body.

The global model, shown schematically in FIG. 5, was formed by integrating the regional circulation parameters with the models of local regions. In the model of the parent, contrast agent was assumed to be injected through an antecubital vein, mixed in the right heart, distributed throughout the body and excreted by the kidneys according to the glomerular filtration rate.

The residence time of contrast agent in an organ was estimated by the time duration of the contrast agent in the capillaries and ECF spaces. The residence time depends on the size of these spaces as well as the transcapillary exchange rate. When a substance is confined to a blood vessel, the circulation time is measured by injecting rapidly a dye or radioactive tracer into a peripheral vein and detecting the moment when it arrives at a sampling site. The volume of a blood vessel travelled by a substance is calculated by multiplying the volumetric flow rate and the circulation time. The mean circulation time from the antecubital vein to the right atrium is approximately 6.9 seconds in an average adult. The time can range from 3 to 14 seconds. This is the temporal difference between the antecubital and the right atrial injections.

Intravascular contrast agents are eliminated from the body mainly by the kidneys. The process is rapid with approximately 50% of injected contrast agent being excreted within two hours presuming normal renal function. The total excretion rate of contrast agent is obtained by multiplying the plasma concentration with a glomerular filtration rate, usually about 19% of renal plasma flow. Peak renal excretion is closely related to peak plasma concentration, because renal plasma flow is relatively constant.

Regional blood flow is expressed according to the magnitude and direction of the flow. For example, the cardiac output is 6500 mL/min., directed away from the right heart. In FIG. 5, the right and left heart are represented by boxes by denoting well stirred compartments. Each blood vessel is represented by a circle surrounding a number which represents its volume in milliliters. Large blood vessels are further divided into multiple smaller compartments in series, typically 20 ml for arteries, and 100 mL for veins: the volume of systemic veins is about 4 to 5 times that of associated arteries. This division scheme in large vessels is rather arbitrary and was based on computational convenience. However, the total blood volume in a given blood vessel closely followed known physiological values.

In FIG. 5, each organ is shown as a box split into two sub-compartments, the upper number denoting intravascular (capillary) volume and the lower number denoting extracellular fluid volume. The concentration of contrast agent in an organ is determined by the ratio of the total mass to the total volume of contrast agent within that organ. The total mass of contrast agent within an organ is calculated by summing the products of the concentrations and the volume in the intravascular and extracellular spaces. The organ volume is obtained by adding the intravascular (IV), extracellular (EC) and intracellular (IC) volumes.

A total of 104 ordinary differential equations were used to describe the cardiovascular model of the parent. These equations were solved using the numerical integration programs of the fifth order Runge-Kutta method on a personal computer. Using a power Macintosh or IBM PC the computation took a few seconds to compute. The contrast concentration curve over time was calculated for each region by solving differential equations of the model for a given contrast injection protocol and a hypothetical patient with variable weight, height, gender and age.

Figure 6:
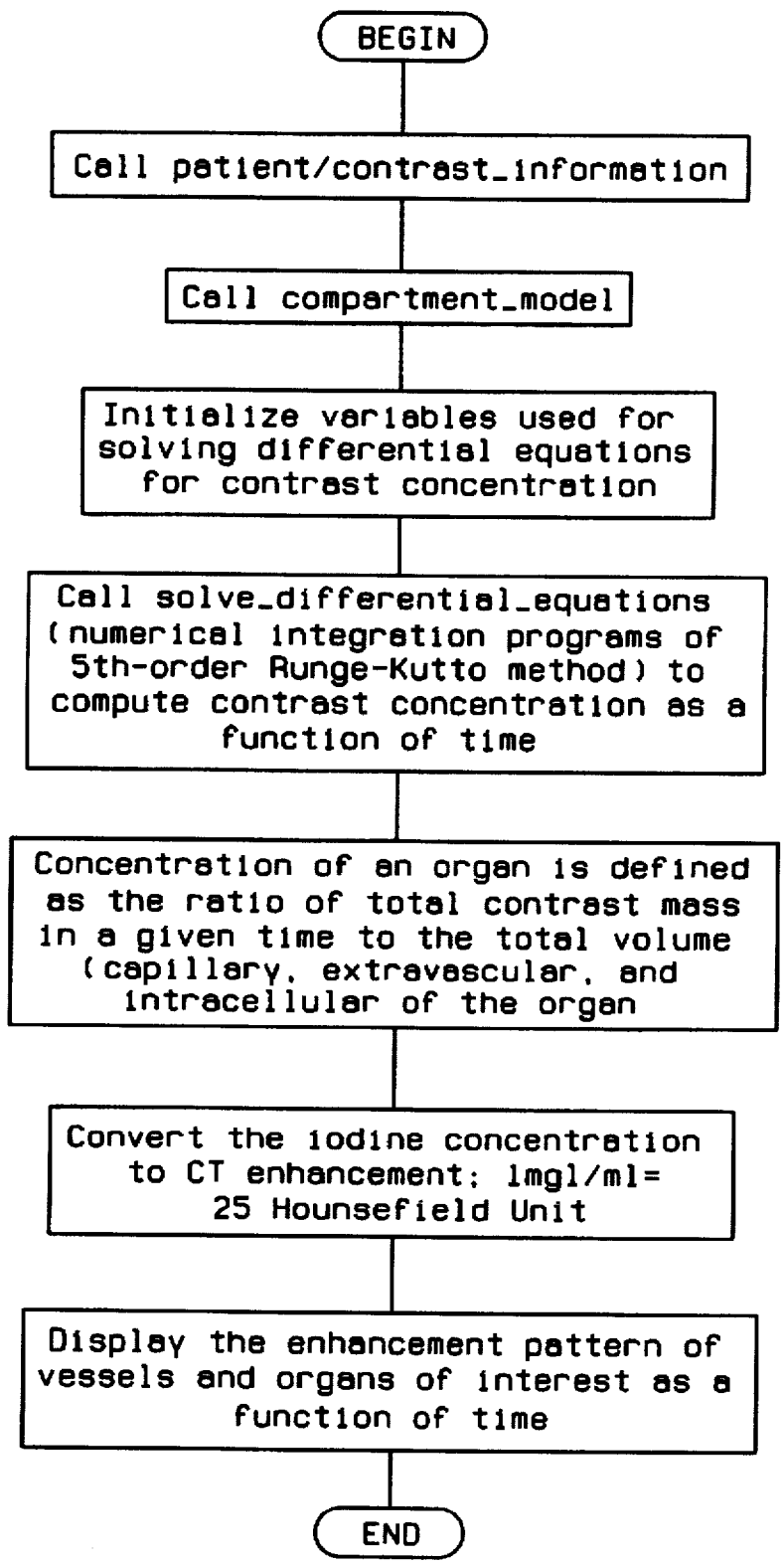
FIGS. 6 is a flow chart showing the method steps for determining predicted contrast enhancement level.
Figure 7:
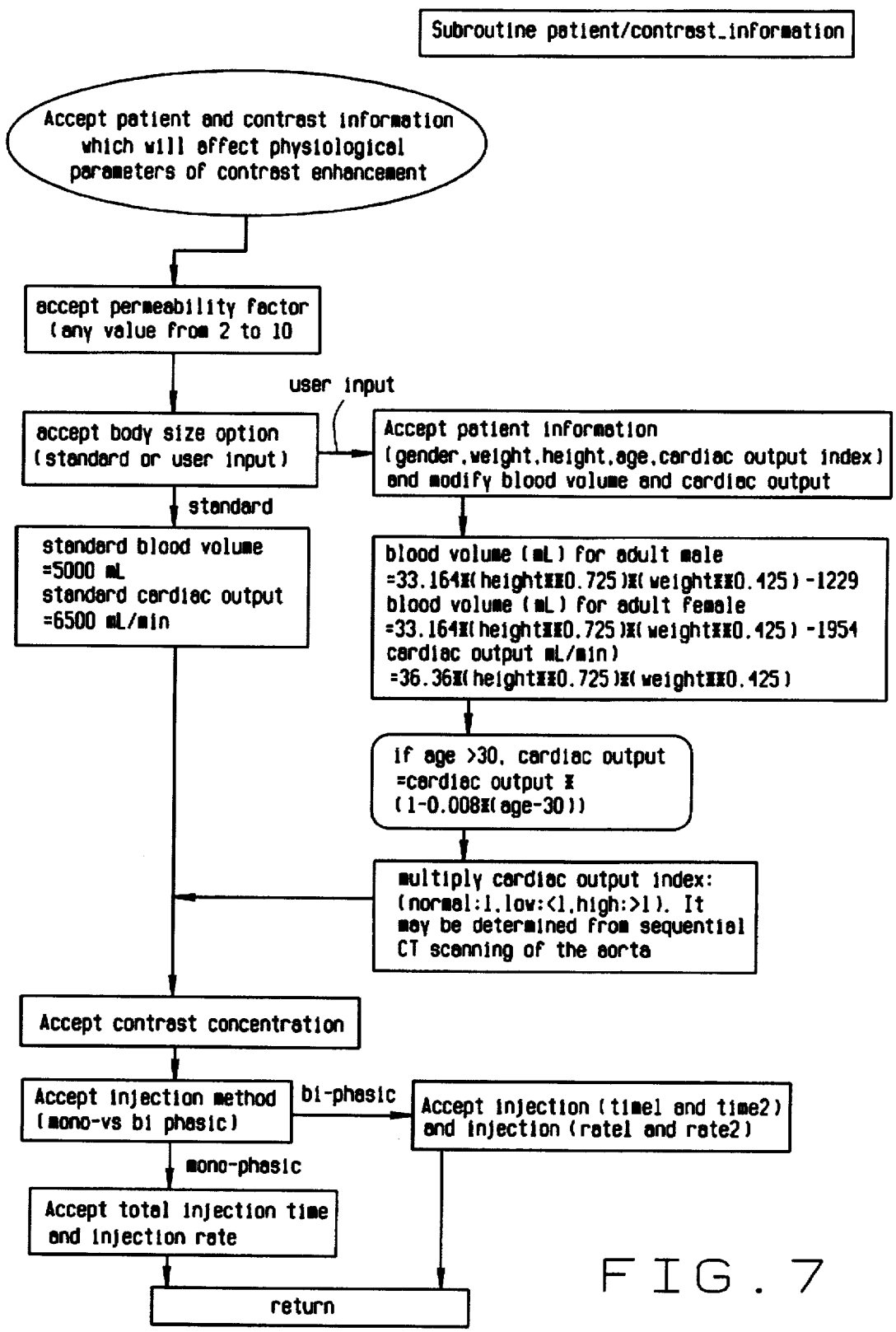
FIG. 7 is a flow chart of a subroutine of the method of FIG. 6 for operator designation of patient information and contrast protocol information.

Referring to FIG. 6, the method of the parent is shown as a flow chart. The first step in the method is to call the patient/contrast information subroutine shown in FIG. 7. This subroutine accepts operator input of patient and contrast information which will affect physiological parameters of contrast enhancement. First, a permeability factor with a range from 2 to 10 is input. Guidance for selection of an appropriate permeability factor is given, infra. However, the inventor has found that acceptable results are achieved upon operator selection of any number between 2 and 10. Next, a body size option is input. At this point, the user has a choice to use a standard model which will include a 5,000 milliliter blood volume and standard cardiac output of 6500 ml/min or a user may input specific information. If specific information is input, the standard blood volume and standard cardiac output are adjusted to conform to the patient's specific information. Blood volume (BV) and cardiac output (CO) can be predicted from the weight (W) in pounds and height (H) in inches of a patient using regression formulae available in standard cardiovascular physiology references. The formula for an adult male with a weight (W) ranging from 100 to 310 pounds, and a height (H) ranging from 60 to 74 inches is:

$$BV = 33.164 * H^{0.725} * W^{0.425} - 1229.$$

For an adult female with weight (W) ranging from 80 to 290 pounds and height (H) ranging from 60 to 74 inches the formula is:

$$BV = 34.85 * H^{0.725} * W^{0.425} - 1954.$$

For an adult male or female, the cardiac output (CO) is given by the formula:

$$CO = 36.36 * H^{0.725} * W^{0.425}$$

In the model of the parent, an adjustment to these variables was made as follows. The ratio of the predicted blood volume to the standard blood volume was calculated. This ratio was then applied to the regional blood volume and extravascular fluid volume in the cardiovascular model so the entire body fluid volume was corrected. The cardiac output and regional blood flow were also modified in the same fashion. Consequently, the regional blood flow, blood volume, and distribution of body fluid in the model can be adjusted for subjects of different body weight, height, and gender.

Cardiac output can be further adjusted based on age using the formula:

$$CO = 6500 \text{ ml/min} * (1 - 0.008 * (\text{age} - 30)).$$

When inputting patient specific information, a choice can be made to further adjust the cardiac output for normal, low, and high. The cardiac output level can be estimated using sequential CT scanning of the aorta.

Figure 8:
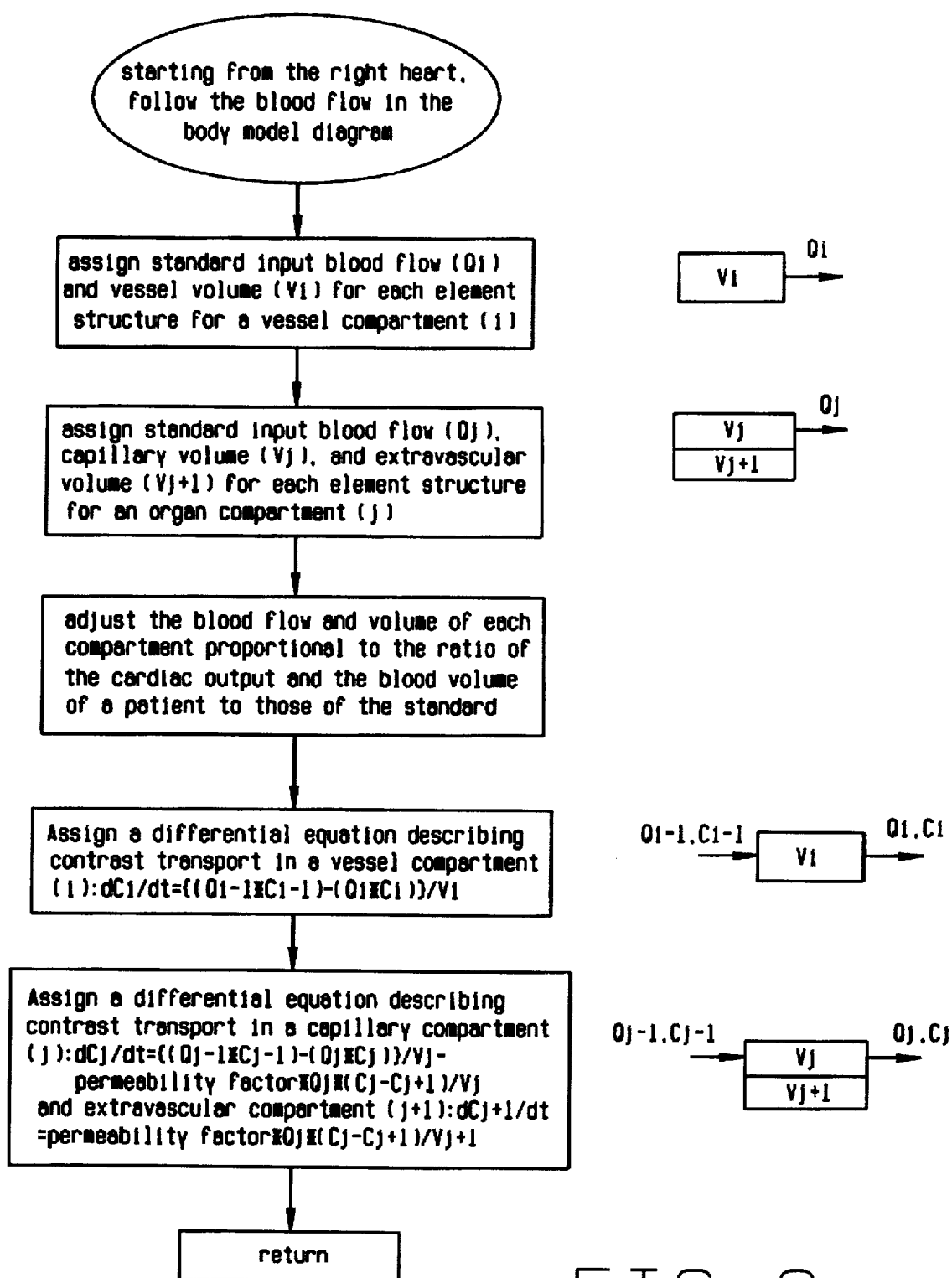
FIG. 8 is a flow chart of a subroutine of the method of FIG. 6 which assigns a differential equation to each element of the cardiovascular model.

Next, a contrast agent concentration is input and accepted as well as an injection method, total injection time, and injection rate. These values are all well known to those of ordinary skill in the art for particular types of CT scans. Thereafter, control is returned to the main program. The second step of the method is to call the compartment/model subroutine. This subroutine, shown in FIG. 8, begins with the right heart and follows the blood flow in the body model diagram shown in FIG. 5. A standard input blood flow and vessel volume is assigned sequentially for each circle element representing a vessel compartment in FIG. 5. Next, a standard input blood flow, a capillary volume, and an extravascular volume is assigned sequentially for each block element representing an organ compartment in FIG. 5. Thereafter, the blood flow and volume of each vessel and organ compartment is adjusted by the program to be proportional to the ratio of the cardiac output and blood volume of the patient as compared to the standard, as calculated in the patient/contrast subroutine.

In the next step, a differential equation describing the contrast agent transport in each vessel compartment, as derived above, is assigned. If the element is a vessel compartment, a differential equation describing contrast agent transport is assigned. If the element is an organ compartment, two differential equations describing both contrast agent transport in the intravascular compartment and in the extravascular compartment are assigned. Thus, each element in the cardiovascular system is assigned sequentially a differential equation. Control is then returned to the main program.

The next step in the method is to solve the differential equations which were assigned in the compartment/model subroutine to obtain the organ specific concentration. The differential equations are solved with numerical integration programs of the 5th-order Runge-Kutta method to compute contrast agent concentration as a function of time for each compartment.

The concentration of contrast agent in an organ is defined as the ratio of total contrast mass at a specific time to the total volume of the organ. Contrast concentration is converted to CT enhancement in Hounsefield Units (HU) using the ratio 1 milligram I/ml=25 HU. The relationship between CT enhancement in HU and concentration of contrast agent in mg/ml depends upon multiple factors including the type of contrast agent, the surrounding tissue and other factors related to the CT scanner such as peak kilovolts used ($kV_p$). The assumed relationship of 1 mg/ml equals 25 HU was arrived at through an experiment comparing CT attenuation and contrast concentration.

Figure 9:
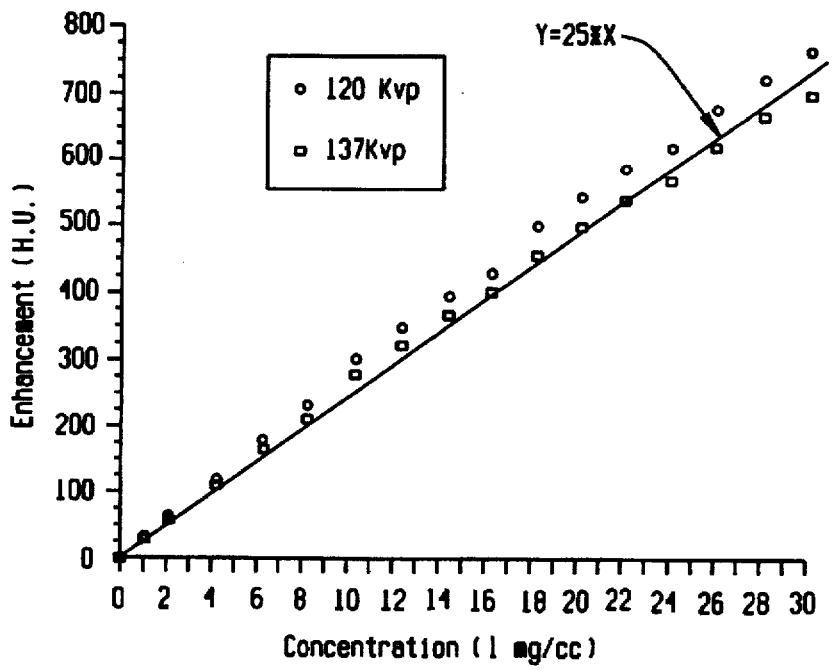
FIG. 9 is a graph showing the linear relationship between enhancement in Hounsefield Units (H.U.) and concentration of Iodine (I mg/ml)

In that experiment, Ioversol-320 (I) was diluted with saline to generate various concentrations ranging from 0 to 30 mg/ml. Fifty ml deposits of the solutions were placed in plastic jars and scanned with a Siemans Somatom Plus CT scanner using standard abdomen and chest settings of 120 $kV_p$ and 137 $kV_p$. CT attenuation was recorded by placing a 1.5 centimeter circular region of interest in the center of each jar on each image. Enhancement was computed as the difference between CT attenuation in each jar and the CT attenuation in a jar filled with normal saline. FIG. 9 is a graph showing the recorded enhancement levels ranging from 8 to 800 HU for concentrations ranging from 0 to 30 mgI/ml at each of 120 $kV_p$ and 137 $kV_p$. When a linear relationship was assumed, an increase in concentration by 1 mgI/ml yielded an approximate increase in contrast enhancement of 25 HU.

The last step in the method shown in FIG. 6 is providing a display of the enhancement pattern of the vessels and organs of interest as a function of time. This can be through either a data stream or a graph.

To gauge the accuracy of the invention of the parent, simulated graphs were generated for a hypothetical patient using different injection protocols. These simulated graphs were compared to empiric graphs representing actual enhancement level measurements in patients who had undergone contrast enhanced CT scans. The empiric graphs represent an average of the recorded enhancement levels in the aorta and liver from three groups of 25 to 28 patients for the injection protocols listed in Table 6 below. Each injection consisted of 125 milliliters of Ioversol-320. The data used to create the empiric enhancement graphs was collected in an unrelated experiment regarding enhancement levels and both uniphasic and biphasic injection protocols. A biphasic injection uses two injection rates during the injection time. A uniphasic injection uses one injection rate during the injection time.

Figure 10A:
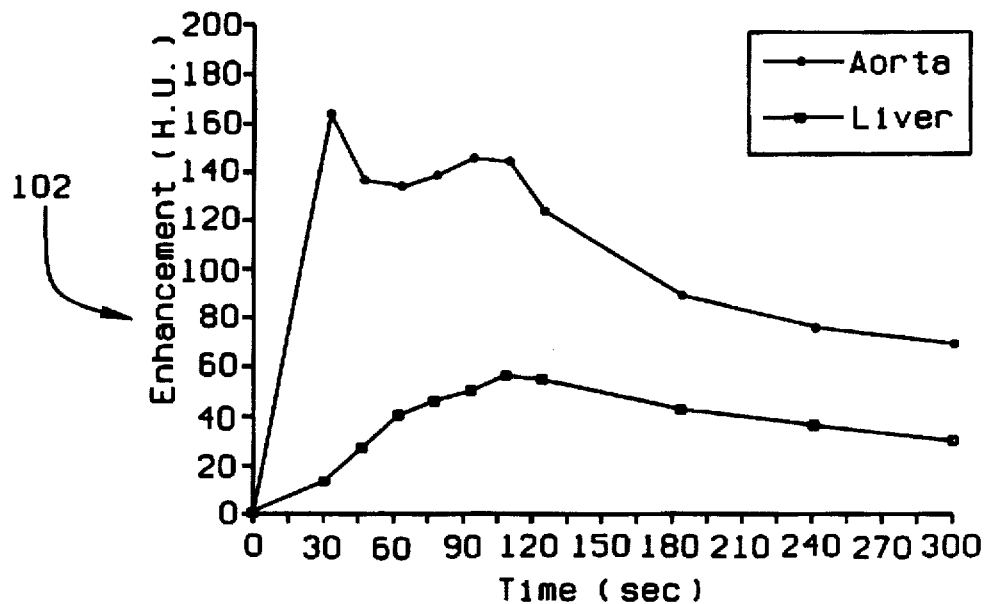
FIG. 10 is a graph showing simulated (10b) and empiric (10a) aortic and hepatic enhancement using the biphasic-low flow rate injection protocol given in Table 6.
Figure 10B:
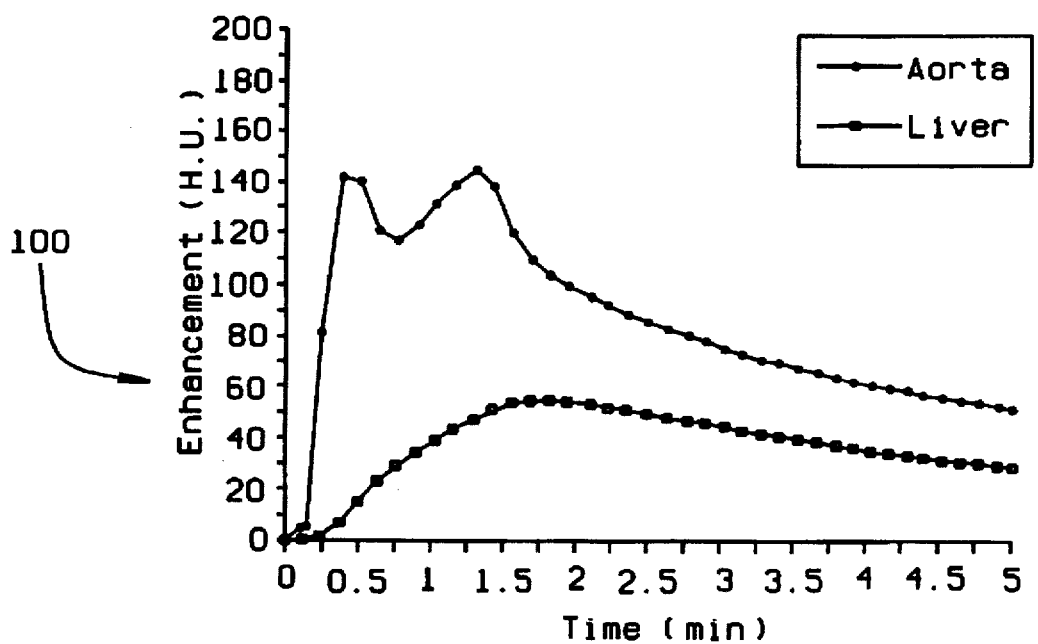

The simulated graphs represent contrast enhancement for each of the three protocols in Table 6 based on a hypothetical patient whose weight equalled the average weight of the corresponding empirical group of patients. Thus, each point on the empiric graphs represents an average of a wide range of empirical enhancement values while each point in the simulated graphs represents a single enhancement value for a hypothetical patient. FIG. 10 shows a simulated graph 100 and an empiric graph 102 for the biphasic-low flow rate injection protocol shown in Table 6. The hypothetical patient, whose enhancement levels are represented in the simulated graph 100, had an assumed body weight of 158 pounds. This assumed body weight was equal to the average body weight of the 28 patients whose actual mean enhancement levels are represented by the empiric graph 102.

Figure 11A:
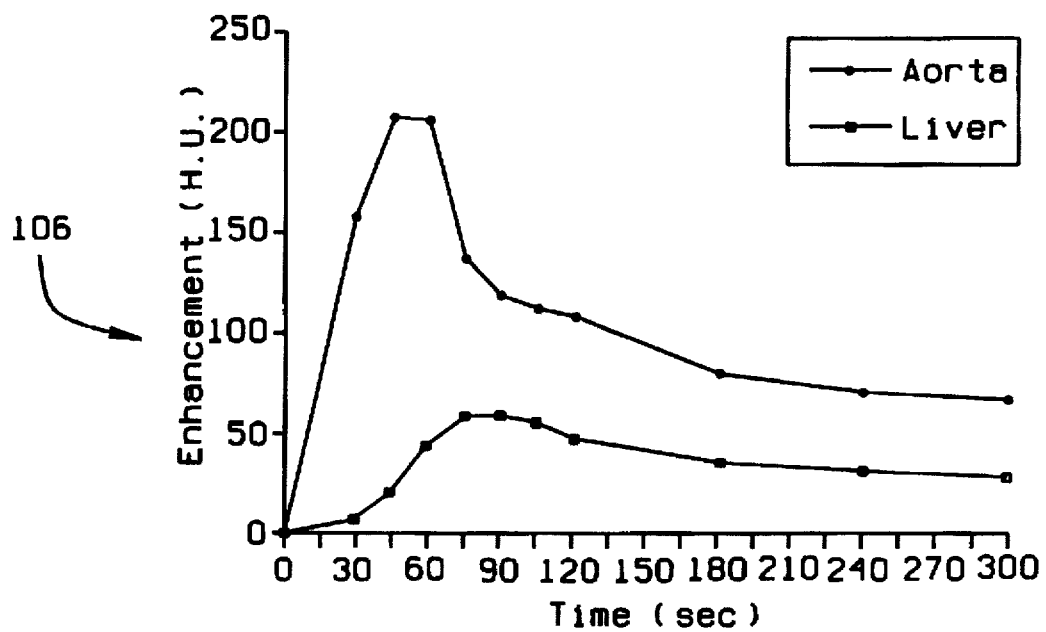
FIG. 11 is a pair of graphs showing simulated (11b) and empiric (11a) aortic and hepatic enhancement using the uniphasic-low flow rate injection protocol given in Table 6.
Figure 11B:
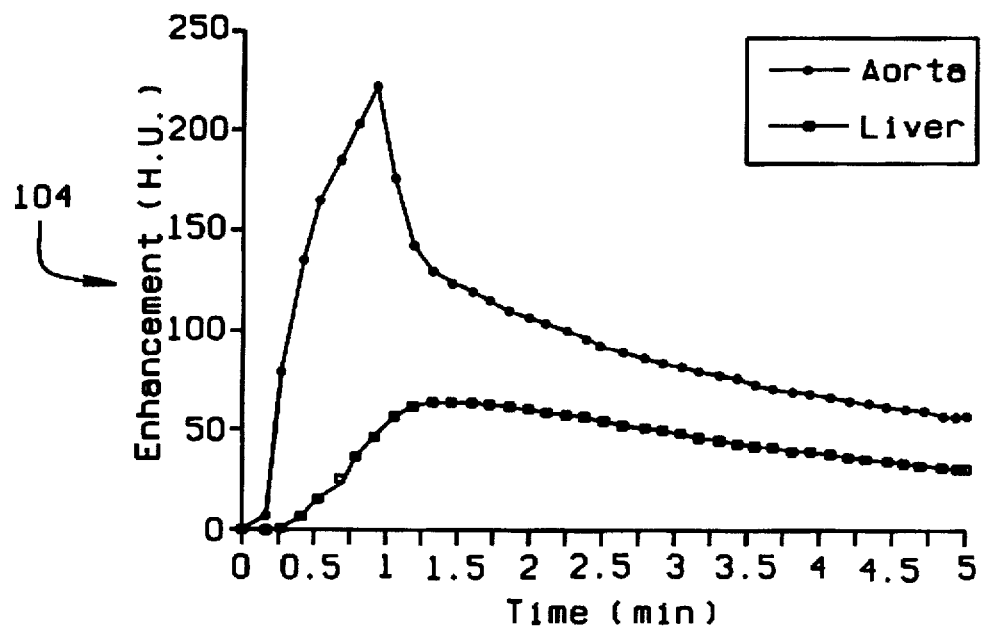

FIG. 11 shows a simulated graph 104 and an empiric graph 106 for the uniphasic-low flow rate injection protocol in Table 6. The hypothetical patient, whose enhancement levels are represented in the simulated graph 104, had an assumed body weight of 171 pounds. This assumed body weight was equal to the average body weight of the 25 patients whose actual mean enhancement levels are represented by the empiric graph 106.

Figure 12A:
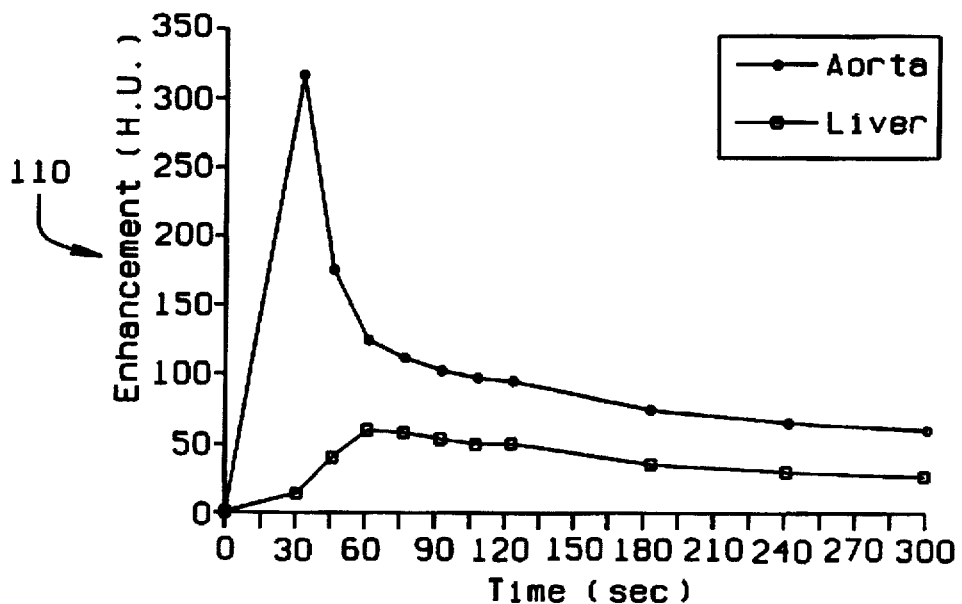
FIG. 12 is a graph showing simulated (12b) and empiric (12a) aortic and hepatic enhancement using the uniphasic-high flow rate injection protocol given in Table 6.
Figure 12B:
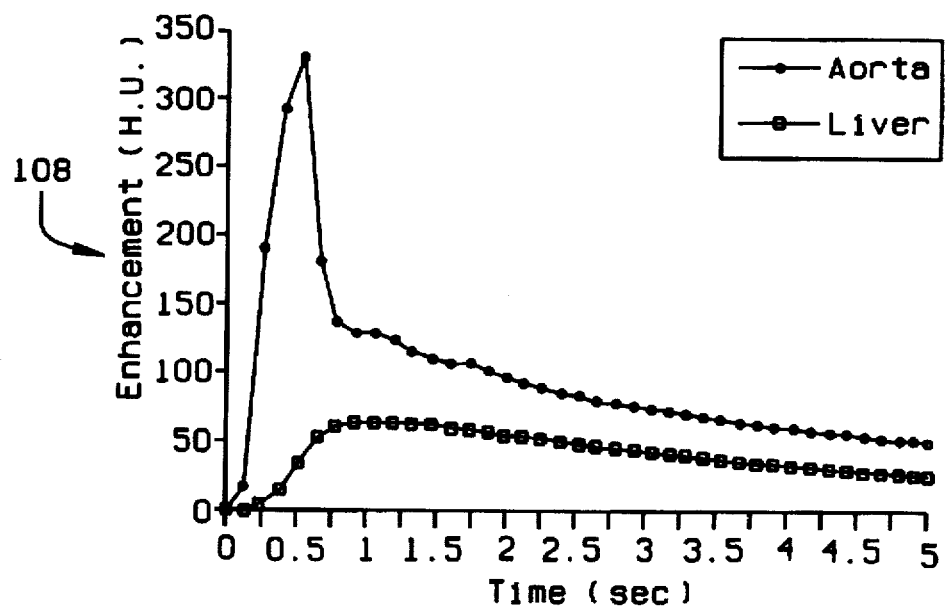

FIG. 12 shows a simulated graph 108 and an empiric graph 110 for the uniphasic-high flow rate injection protocol in Table 6. The hypothetical patient, whose enhancement levels are represented in the simulated graph 108, had an assumed body weight of 177 pounds. This assumed body weight was equal to the average body weight of the 27 patients whose actual mean enhancement levels are represented by the empiric graph 110.

The simulated and empirical contrast enhancement graphs were compared according the maximum enhancement level of each graph and the percent difference between the graphs. The simulated graphs were in good agreement with the empiric graphs. For example, in FIG. 10, for the biphasic-low flow rate injection protocol the simulated maximum aortic enhancement was 142.7 HU while the empiric maximum aortic enhancement was 163.4 HU. Also in FIG. 10, the simulated maximum hepatic enhancement was 53.8 HU while the empiric maximum hepatic enhancement was 55.5 HU.

In FIG. 11, for the uniphasic-low flow rate injection protocol, the simulated maximum aortic enhancement was 220.4 HU while the empiric maximum aortic enhancement was 205.8 HU. Also in FIG. 11, the simulated maximum hepatic enhancement was 63.8 HU while the empiric maximum hepatic enhancement was 59.8 HU.

In FIG. 12, for the uniphasic-high flow rate injection protocol the simulated maximum aortic enhancement was 321.3 HU while the empiric maximum aortic enhancement was 313.7 HU. Also in FIG. 12, the simulated maximum hepatic enhancement was 63.6 HU while the empiric maximum hepatic enhancement was 60.8 HU.

The total mean difference in maximum enhancement between the simulated and empiric graphs was 7.4 percent for aortic enhancement and 4.8 percent for the hepatic enhancement. As can be seen in FIGS. 10, 11 and 12, the simulated and empiric graphs were also nearly identical in variation over time. Specifically, the average enhancement difference between the simulated and empiric graphs for all three protocols in Table 6 was 11.6 percent for aortic enhancement and 12.7 percent for hepatic enhancement.

Figure 13A:
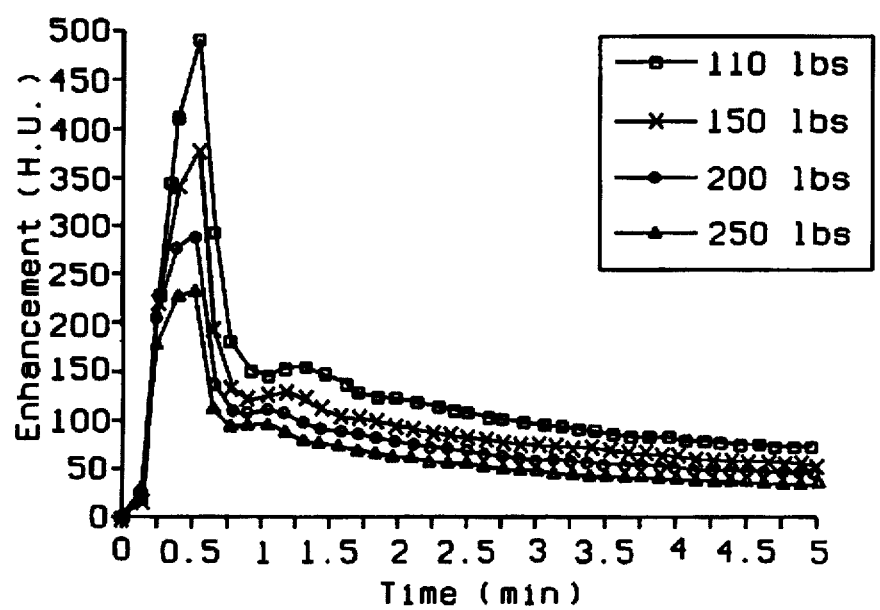
FIG. 13 is a graph showing simulated aortic and hepatic enhancement curves generated by the invention of the parent for hypothetical patients weighing 110, 150, 200 and 250 pounds.
Figure 13B:
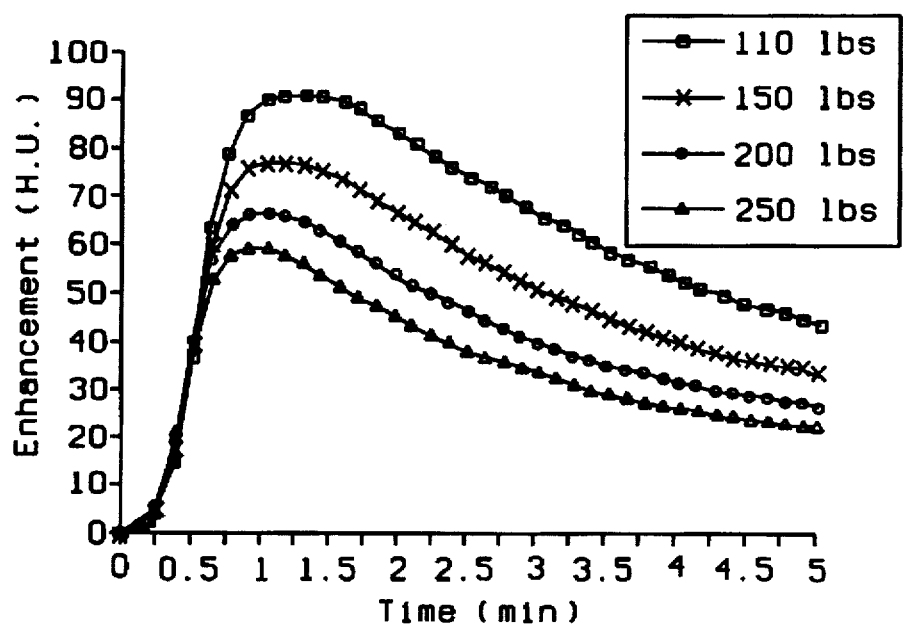

It is well known that body weight is one of the patient variables which most drastically affects contrast enhancement. To confirm the functionality of the invention of the parent, the effect of body weight on contrast enhancement was simulated in a hypothetical patient. FIG. 13(a) shows simulated aortic enhancement graphs and FIG. 13(b) shows simulated hepatic enhancement graphs for uniphasic-high injection protocol in an adult male with a fixed height (5'8") and body weights of 110, 150, 200 and 250 pounds. The simulated graphs demonstrate that contrast enhancement was greatly affected by body weight. For example, in FIG. 13(a), the peak aortic enhancement in a subject weight 110 pounds was more than twice that in a subject weighing 250 pounds. However, as expected, the timing of the aortic and hepatic peaks did not vary significantly because alteration in the cardiac output was compensated by alteration in the blood and body fluid volume. The simulated graphs in FIG. 13 correlate well with empiric observations in patients showing an inverse relationship between body weight and contrast enhancement.

In the patient/contrast subroutine, selection of a permeability factor between 2 and 10 is required, as explained, infra. However, of the variables used to construct the cardiovascular model of the parent, the least is known about the transcapillary permeability. Permeability varies from organ to organ and depends, in part, on the substance being transferred. Organs with discontinuous capillaries such as the liver, spleen and bone marrow have relatively high permeability. Fenestrated capillaries in the kidney and intestines have intermediate permeability. Continuous capillaries in the heart muscle and skin have smaller pores and thus lower permeability.

Although, some general information about permeability is known, knowledge about specific transcapillary permeability is limited. For example, the size of the contrast substance is one of the most important properties in determining the rate of transcapillary exchange. Permeability for different substances will vary according to each substance's molecular weight. Most nutrients and metabolites including glucose (mw=180) and sucrose (mw=342) are quite readily diffusible.

When transcapillary exchange occurs slowly relative to the blood flow rate, it is primarily diffusion-limited. Conversely, if transcapillary exchange occurs rapidly relative to the blood flow rate, it is primarily flow-limited. Iodinated contrast agents consist of relatively small molecules with molecular weights between 800 and 1600. Such contrast agents are distributed rapidly and extensively outside the blood vessels to the entire extracellular fluid within a few minutes of injection and are highly diffusible. Therefore, in the model of the parent, it was assumed that the transport of contrast agents to be mostly flow-limited and this assumption was applied equally to every organ in the cardiovascular model.

Figure 14A:
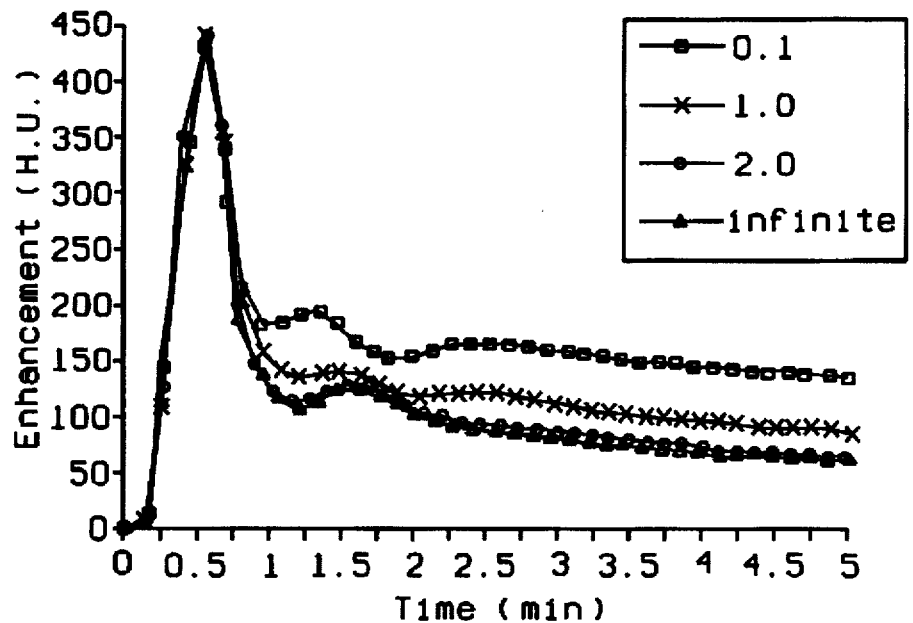
FIG. 14 is a graph showing simulated aortic (14a) and hepatic (14b) enhancement curves for permeability (PS) values of 0.1, 1.0, 20 and infinity.
Figure 14B:
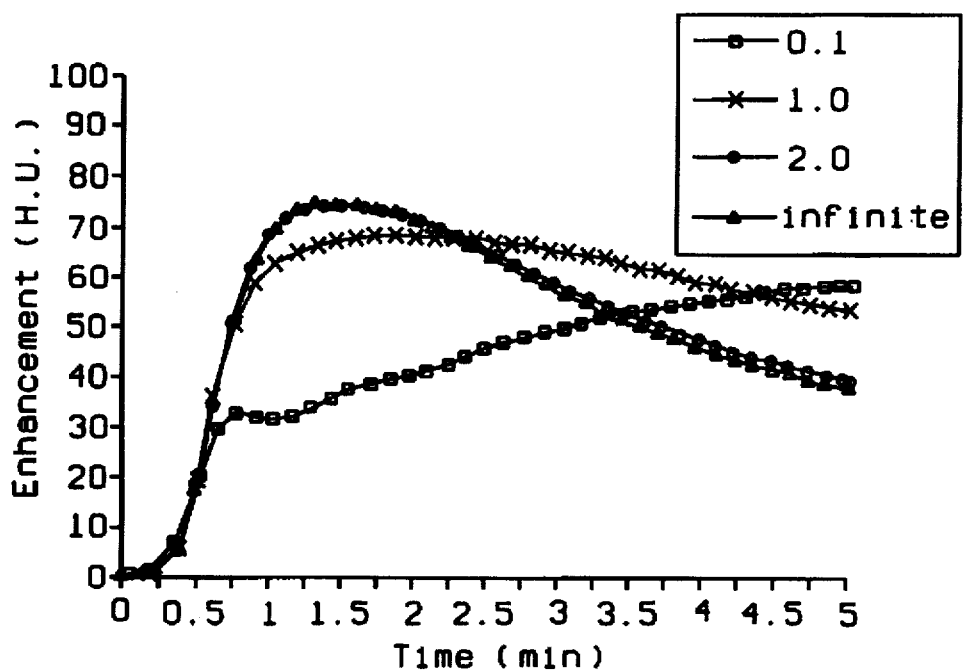

Permeability (P) and transfer area (S) are usually treated as a unit because of the difficulty evaluating them separately without very detailed anatomical information. The permeability-surface area product (PS) is referred to as the "capillary transport coefficient." The magnitude of PS in an organ is frequently expressed relative to the blood flow rate, Q. If PS/Q is larger than 1, the transport is flow-limited. If PS/Q is less than 1, it is diffusion-limited. In an effort to determine acceptable PS values in the model of the parent, simulated CT enhancement graphs were generated for several different PS/Q values. The simulated graphs are shown in FIG. 14(a) for aortic and FIG. 14(b) for hepatic for PS/Q values equal to 0.1, 1, 2, 20 and infinity.

Simulated graphs were also generated assuming no transcapillary barrier between the capillary and extracellular spaces, i.e., a single compartment representing each organ. The simulated CT enhancement graphs generated by the invention of the parent with PS/Q=20 closely approach those obtained by ignoring the transcapillary barrier. Thus, this PS/Q value is near the upper limit of flow-limited capillary transport. The simulated graphs shown in FIGS. 14(a) and 14(b), when compared with empiric graphs, confirm that the transport of contrast agent follows a flow-limited process, especially in richly perfused tissues.

Figure 16:
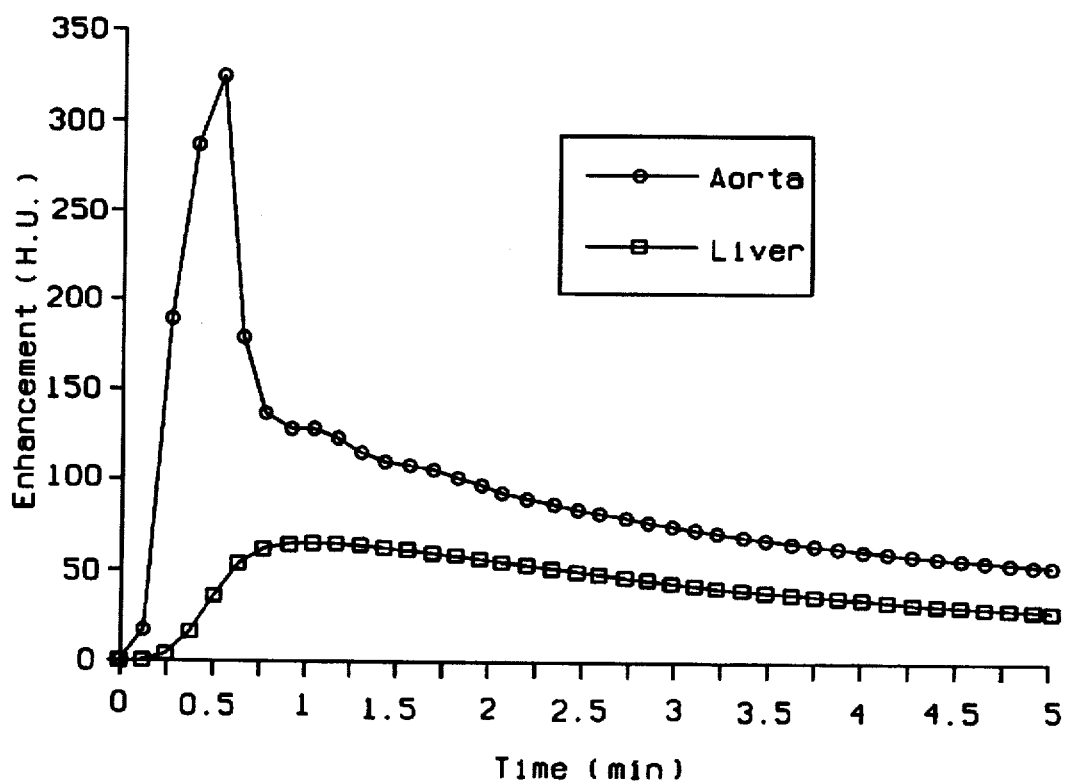
FIG. 16 is a graph output generated by the invention of the parent showing predicted aortic and hepatic enhancement levels versus time using the data in FIG. 15.

FIGS. 15 and 16 show sample aortic and hepatic enhancement levels generated by the invention of the parent in data format and graph format, respectively. Operation of the invention of the parent can be best understood by referring to FIG. 15. Prior to performing a CT scan, an operator inputs the patient specific information, such as height weight and cardiac output, and an injection protocol into the program in accordance with the above description of the invention of the parent. The program then generates output data showing the predicted organ specific enhancement values as a function of time. The output data can take the form of a data stream as shown in FIG. 15 or a graph as shown in FIG. 16.

The operator views the data initially to determine whether the proposed injection protocol will result in an acceptable enhancement level for an acceptable duration. If the data shows that the desired enhancement level will never be reached, or will not be sustained for a sufficient length of time, the operator chooses a different injection protocol and then reruns the program until a satisfactory predicted enhancement level is obtained.

After the operator obtains an output showing an acceptable predicted enhancement level and duration, the operator then selects a scan start time and duration, including an appropriate collimation thickness and table speed. In the alternative, all or a portion of the selection can be performed by the computer. This information is then input into the CT scanner, if obtained off-line from the CT control computer, and the scan is then executed. For example, assuming a threshold hepatic enhancement level of 50, the data of FIG. 15 shows that the threshold enhancement level is not reached until 0.64 minutes after the injection of contrast agent into the patient. In addition, the data shows that the threshold enhancement level will be maintained for approximately 1.7 minutes. Using this information, an operator inputs the scan start time, scan duration, collimation thickness and table speed into the CT scanner and thereafter performs the scan on the patient. In the alternative, computer software can be implemented to automatically transmit the output information directly into the CT scanner.

The program of the parent gives an output which includes a predicted enhancement level in the tissue of interest as a function of an elapsed time after injection. As discussed above, the enhancement threshold is a level of tissue enhancement below which results in a poor quality scan. The scan duration is the time between starting the scan and ending the scan. In order to optimize the scan, the tissue scanned must maintain an enhancement level equal to or greater than the threshold enhancement level for the entire scan duration.

The inventors herein have further expanded the invention of the parent by providing a means for analyzing the generated predicted enhancement function (enhancement level with respect to time) to determine if the predicted enhancement level in the tissue to be scanned sufficiently meets the criteria required for an optimum scan and providing a means for adjusting the injection protocol until the output is acceptable.

In the preferred embodiment, preferably implemented in a computer program, if the output predicted enhancement function indicates that the tissue enhancement level will never attain the desired enhancement threshold or that the tissue enhancement level will not be maintained above the desired threshold for a period of time equal to or exceeding the scan duration, the program provides a means for adjusting the injection protocol.

Figure 18:
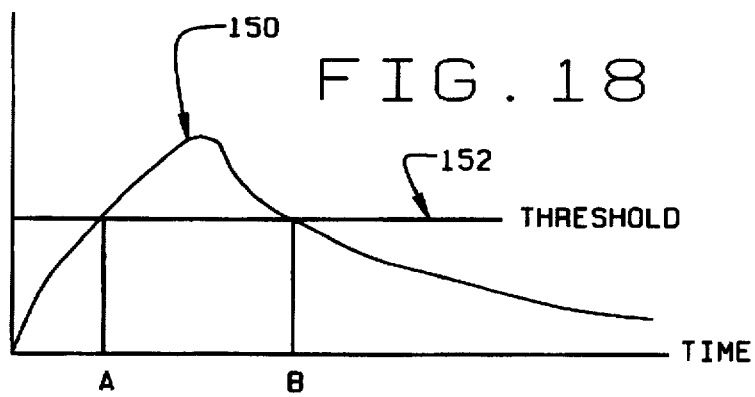
FIG. 18 is a graph output generated by the present invention showing the predicted enhancement function versus time superimposed over a line representing a threshold enhancement level.

Referring to FIG. 18, the output of the preferred embodiment is a graph or curve 150 showing a predicted enhancement level as a function of time superimposed on a line 152 representing the enhancement threshold. When the peak enhancement, the highest level reached by curve 150, is below the desired threshold, or when the time interval (B−A) is shorter than the desired scan duration, enhancement level must be raised to obtain an acceptable scan. In the graph of FIG. 18, enhancement curve 150 exceeds the enhancement threshold for time period (B−A).

If the peak enhancement does not reach the threshold or if the time interval (B−A) is not equal to or greater than the desired scan duration, the preferred embodiment provides the operator two options to increase the predicted enhancement level. It is known in the art that increasing contrast volume, flow rate, or concentration increases the level of enhancement. Because enhancement level is a function of the amount of contrast transported through a particular tissue over a given time period, increasing flow, volume and concentration all result in increased enhancement levels. In the majority of the injector systems, volume and flow rate are easily adjusted through the injector system controls. In addition, most medical facilities have a limited number of differing concentrations. Therefore, the most practical adjustments to adjust enhancement levels are to volume and flow rate. However, adjusting concentration is also acceptable to raise enhancement.

Figure 21:
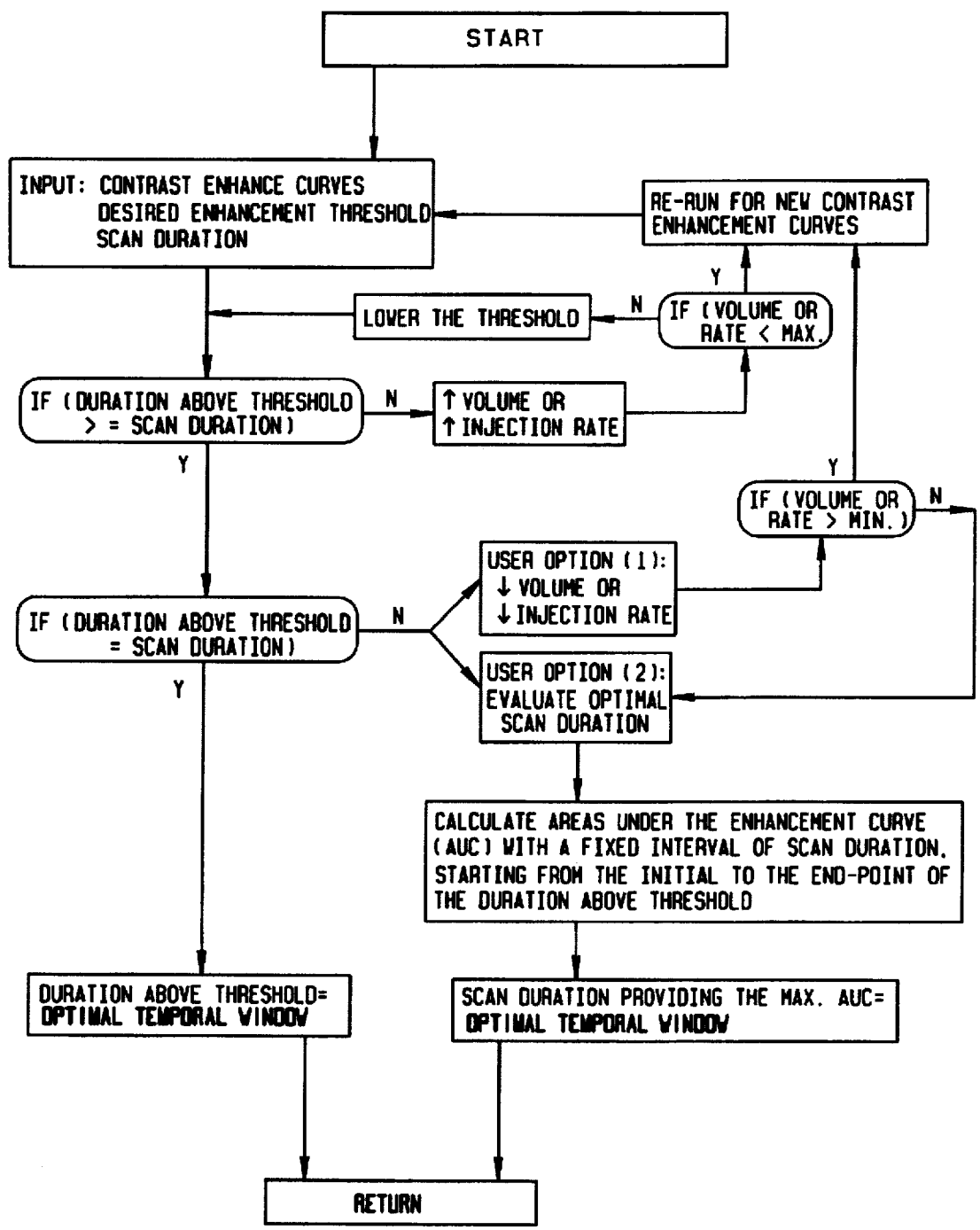
FIG. 21 is a flow chart showing the method steps of the present invention used to calculate an injection flow rate and volume which provide a predicted enhancement function which exceeds a threshold value for a period greater than the scan duration and the method steps to select an optimum scan interval within the period.

The steps of this aspect of the preferred embodiment are shown in the flow chart of FIG. 21. After receiving an input of a predicted contrast enhancement function, an enhancement threshold and a scan duration, the program determines if the predicted enhancement function exceeds the threshold for a time period greater than the scan duration. If not, the operator has the option of either (i) increasing the contrast volume or (ii) increasing the flow rate. After receiving new volume, flow rate or both, the program determines if the maximum allowable flow rate or maximum allowable volume have been reached. It is known in the art that injection flow rates and volumes have maximum limits above which safety concerns are implicated. These limits vary depending on many factors including the particular patient, the contrast agent and the particular procedure involved. Therefore, the present invention provides for the input of maximum values for flow rate and volume. When either the maximum allowable contrast volume or injection rate is reached without achieving the threshold enhancement level, the program continues to allow increasing the other until both maximums are reached. After input of new values, the program iterates the steps of updating the predicted enhancement function based on new values. The contrast volume or the flow rate is progressively increased in this fashion until the time interval (B−A) becomes equal to or greater than the requested scan duration.

In the preferred embodiment, once the volume and flow rate have reached the maximum values, and the predicted enhancement function does not exceed the threshold for a time period greater than or equal to scan duration, the program notifies the operator that a new enhancement threshold must be chosen.

Although the preferred embodiment allows the operator to input different flow rates and volumes, the entire process could be automated and performed by a computer processor. For example, as an alternative to the operator selecting the flow rate and volume to obtain an acceptable enhancement level, a linear bisection method, or other known mathematical process, could be programmed into the computer to solve for a convergence point by reducing the differences between and updating two boundary values.

Although a variance in cardiac output may affect the level of enhancement in a given tissue, the inventors herein have discovered that a change in cardiac output will more dramatically affect the time at which a particular level of enhancement will be achieved. However, the program selects a cardiac output believed to be most closely associated with the patient and uses that value in its computation of the predicted enhancement function. The program also provides for operator input of alternative values for cardiac output with each resulting enhancement function being tested using the above described method. In this way, an operator can be certain that a specific injection protocol will result in a predicted enhancement function which exceeds the desired threshold for the entire scan duration regardless of the cardiac output of the patient.

As shown in the flow chart of FIG. 21, when the predicted duration of the enhancement (B−A) is greater than the requested scan duration, the method of the present invention allows the operator to select from the options of (i) reducing the volume of the contrast medium or (ii) reducing the injection rate; or (iii) maintaining the current enhancement level and searching for the optimal scan interval within A and B. Options (i) and (ii) may be used for a more efficient scan or for reasons related to a patient's medical history. For example, by reducing the volume of the contrast medium, costs are saved and the patient need not be given unnecessary additional contrast to create an acceptable scan. Because the contrast medium might have side effects on the patient, reducing the amount of contrast may be desired to limit the amount of contrast a patient must receive in order to undergo a successful CT scan.

As shown in the flow chart of FIG. 21, the process steps of decreasing the volume and/or rate are virtually identical to the method of increasing these values, except for the direction of adjustment, and the discussion above related thereto is equally applicable here. It is also foreseeable that the process steps for increasing and decreasing the flow rate and/or volume could both be utilized in one scan procedure, if for example, an adjustment in one direction resulted in too great a change in enhancement level or, after lowering the threshold, the enhancement level is predicted to exceed the revised threshold for an excessive period.

In the alternative, or if the above concerns are not a factor, as mentioned above in option (iii) the preferred embodiment allows the option of maintaining the selected injection protocol and determining the optimum interval between time A and time B which is equal to the scan duration and during which the tissue enhancement level is the greatest. The method of the parent was a significant improvement over the prior art in that it allowed prediction, prior to injection, of whether the enhancement level would exceed the threshold value or whether modifications were required in the various input parameters to obtain a tissue enhancement level which exceeded the threshold value for the scan duration. In this fashion, an operator can determine the proper delay after initiating the injection to begin scanning as well as an optimum scan duration. This information also enabled the operator to change various scan parameters, including table speed and collimation thickness in order to achieve a scan during the time when the tissue enhancement level exceeded the threshold level.

Under certain circumstances, the predicted tissue enhancement function exceeds the threshold enhancement level for a time period greater than the scan duration. The operator could choose arbitrarily at what point after the tissue enhancement level exceeded the threshold to begin the scan, as long as the scan would be completed before the tissue enhancement level decreased below the threshold level and obtain an acceptable scan. Building further on the invention of the parent, the inventors herein have provided a means for selecting a scan start time to cause the scan to take place during the optimum temporal window between time B and time A if the duration of predicted enhancement above threshold exceeds the scan duration by more than a predetermined amount of time. As shown in the flow chart of FIG. 21, when the time interval (B−A) is equal to (or approximately 10% greater than) the expected scan duration, point A becomes the onset of scanning. Thus, the optimal temporal window of scanning begins at time A and ends at time B. If, however, the time interval (B−A) is significantly greater than the expected scan duration plus 10%, the invention selects an optimal temporal window within B−A by maximizing the predicted enhancement available. This best understood by referring to FIG. 19.

Figure 19:
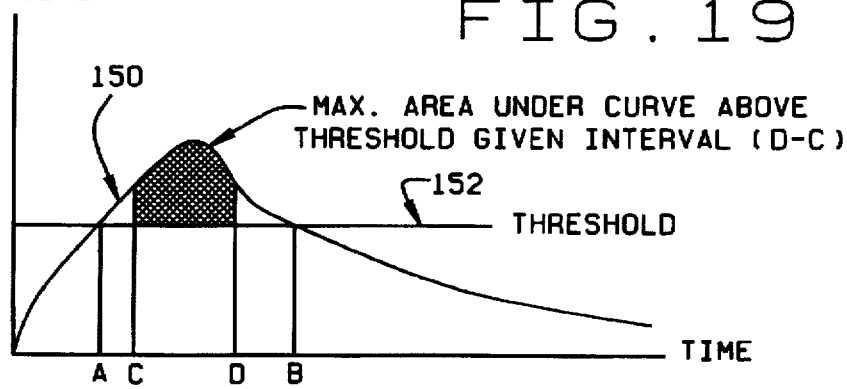
FIG. 19 is a graph output generated by the present invention showing the predicted enhancement function and identifying those intervals for which the predicted enhancement function exceeds the threshold value.

In FIG. 19, the enhancement curve or function 150 of the tissue to be scanned is displayed along with a desired threshold of enhancement 152 on a graph of enhancement versus elapsed time after injection. As shown, the enhancement level of the tissue to be scanned increases from level 0 at time 0 to a level equal to the desired enhancement threshold at time A. The tissue enhancement level continues to rise to a peak enhancement level above the threshold and then decreases to again equal the desired threshold at time B. After time B, the tissue enhancement level continues to decrease below the threshold. As is known in the art, a uniphasic injection results in a single peak enhancement level being attained as shown in FIG. 19. Thus, the duration of predicted enhancement above threshold is represented as (B−A).

Referring still to FIG. 19, the method of the present invention selects two points (C and D) whose difference (D−C) is equal to the scan duration and between which the area under the enhancement curve above the threshold (AUC) is maximized. As executed in one of the steps of the flow chart of FIG. 21, a set of AUC's are calculated as point C incrementally advances with a fixed interval (D−C) to determine the optimum scan interval. The first AUC is calculated when C coincides with A. This would correspond to beginning the scan at the time the tissue enhancement level first equals the threshold value. The last AUC is calculated when D coincides with B. This would correspond to ending the scan when the tissue enhancement level equals the threshold level for the second time. After calculating the set of AUC's, choosing the maximum AUC sets the optimal scan start time (C) and scan end time (D).

The number of AUC's in the set is dependant on the increment with which C is advanced. Of course, the smaller the increment of advancement, the more accurate on average the time interval predicted for optimal scanning will result. The inventors herein have found that calculating the AUC's while incrementally advancing C in units of 1 second is satisfactory. When the enhancement curve is uniphasic, a plot of the set of AUCs demonstrates a similar distribution and the optimal scanning interval contains the peak enhancement point. Thus, in a uniphasic scan the maximum AUC should be known once the calculated AUC begins to decrease from a peak value.

Unlike the prior art, the invention disclosed in the parent allows the operator to predict, prior to starting an injection, whether tissue enhancement will successfully attain a threshold, whether the tissue enhancement level will be maintained above the threshold for the entire scan duration, and the proper scan delay to allow the scan to begin at a time when the tissue enhancement level exceeds the threshold value. The above described improvements enhance the invention of the parent by providing a means for optimizing the injection protocol to obtain acceptable enhancement levels and optimizing the scan start time when the period of acceptable enhancement is predicted to be greater than the scan duration.

These methods and those of the parent are significant improvements over the prior art and allow prediction well within acceptable limits of accuracy. However, the inventors herein have further improved the invention by providing for even more accurate predictions. As explained in the parent, the tissue enhancement level is directly related to the volume and concentration of contrast in the tissue to be scanned when the scan takes place. Because the contrast agent is distributed throughout the patient by the cardiovascular system, the amount of contrast in a given tissue at a given time is related to various patient specific parameters which affect contrast transport throughout the patient. These include height, weight, gender, age, and cardiac output.

Cardiac output, unlike height, weight, gender and age is not readily measured. As explained in the parent, many factors including disease status or prior heart failure may affect cardiac output. In addition, a patient does not maintain the same cardiac output during his or her entire lifetime.

Inputting the correct cardiac output into the model is necessary for accurate prediction of optimum scan delay. For example, if a patient has a poor cardiac output and the operator uses a standard cardiac output because the cardiac status is unknown, the predicted optimum time to begin scanning a tissue will not coincide with the actual optimum time to begin scanning the tissue. Although the predicted threshold level will eventually be mat, the maximum period of enhancement may still not coincide with the period of scanning due to the input of an inaccurate cardiac output.

To account for varying cardiac output, the parent provided for the input of different cardiac output values into the mathematical model of the cardiovascular system. In addition, the invention of the parent provided for the operator to choose several alternative values for cardiac output and generate a family of predicted tissue enhancement functions or curves corresponding to the alternative values. By predicting and analyzing the family of curves prior to injection, the operator could be certain that the tissue enhancement level would meet or exceed the threshold enhancement regardless of the cardiac output.

In the present invention, each family member has a slightly different cardiac output status so that the entire family represents the predicted tissue enhancement functions for the entire spectrum of cardiac output status. Increasing the number of family members increases the accuracy of the prediction for a given patient. For example varying standard cardiac output by 10% between each family member from 10% to 110% will give the predicted tissue enhancement level in ten patients having identical body habitus, except for cardiac output, and the predicted enhancement functions will reflect the difference caused solely by the 10% difference in cardiac output between each patient.

The invention of the parent provides for taking actual measurements of enhancement after initiating the injection and comparing the family of enhancement curves to the actual enhancement curve to determine which family member most closely resembles the actual enhancement levels. In that way, the invention of the parent provides a means for determining early in the scan, before the threshold level had been reached, whether the scan parameters were appropriate and allows for adjustment if necessary.

Although this is a significant improvement over the prior art, the comparison of the family of curves to the actual enhancement measurements in the tissue to be scanned must be performed quickly to allow time to adjust the scan parameters if necessary. Therefore, the present invention uses a combination of a predicted enhancement function, in a region of interest, such as the aorta, prior to injection, and measurements of actual enhancement levels, after initiation of injection, to calculate a correction factor (such as proper cardiac output status) to be used by the model when predicting a tissue enhancement function for the tissue to be scanned, such as the liver. The preferred embodiment provides for sequential low-dose pre-scanning of the aorta after injection to calibrate the mathematical model to unknown or difficult to measure specific patient parameters such as cardiac output. Because the contrast reaches the aorta quicker than the liver, using enhancement level measurements in the aorta as feed back increases the time allowed to make corrections to the scan parameters before the required onset of hepatic scanning.

The preferred embodiment is implemented in a computer program and can be implemented in a stand alone computer, a computer included in a CT scan machine or a computer included in an injector system. Moreover, the present invention could be implemented in a CT scan system which includes an injector and a CT scan machine both controlled by the same computer. In the preferred embodiment, the computer program contains a mathematical model of the patient's cardiovascular system. The details of the mathematical model are fully explained in the parent.

The computer program accepts input values for those parameters in the patient and in the injection protocol which affect contrast transport through the cardiovascular system. These include patient age, gender, height, weight, cardiac output and injection flow rate, volume, concentration, phase and scan duration. The program accepts the inputs and generates a predicted enhancement level as a function of an elapsed time after injection for both aortic and hepatic enhancement. FIG. 20 shows a table giving the data output from the program for a particular patient having a particular body habitus and presuming a standard cardiac output. The operator has already adjusted the injection protocol using the method set forth above to ensure that the predicted enhancement function will exceed the threshold for a length of time exceeding the scan duration. The columns of information displayed in FIG. 20 are as follows: the left most column headed "time" represents elapsed time from the start of injection; the next column to the right displays the calculated predicted hepatic enhancement level in Hounsefield Units; the next column is the difference between the predicted enhancement level and the preselected threshold chosen as 50 Hounsefield Units; and the next column displays the calculated AUC, with each entry being aligned with its corresponding scan start time. For example, the first entry of 9.6 corresponds to a scan start time of 40 seconds and a scan end time of 70 seconds. Using the methodology of the present invention, the maximum AUC is readily identified as 263.8 which corresponds to a scan start time of 60 and a scan end time of 90. The start scan and end scan times for the optimal temporal window are identified in the last column of the table of FIG. 20.

To enhance the prediction of scan start time, the method of the present invention can be used to update or confirm the output of the table in FIG. 20. First, a base line scan is performed at a region of interest prior to the initiation of the injection so as to enable a calculation of the actual enhancement level for the region of interest. The base line scan, as is known in the art, is a low-dose or partial scan in which the x-ray dose is reduced substantially compared to a typical scan and views may be acquired through less than a full revolution of the gantry. The x-ray dose is thus considerably less than a normal image scan, but nevertheless, a slice image may be reconstructed.

In the preferred embodiment, an actual aortic enhancement function is compared with predicted aortic enhancement functions, generated using different cardiac outputs, to calculate a correction factor to be applied to the model before predicting a hepatic enhancement function. After the correction factor is applied, the predicted hepatic enhancement function generated is more accurate than the predicted hepatic enhancement function generated without the correction factor. Although the region of interest monitored can be the tissue to be scanned, it is preferable to monitor a region of interest distinct from, and one which will provide a measured response faster than, the tissue to be scanned to allow for maximum time to calibrate the mathematical model to the particular patient and update the scan parameters. In the preferred embodiment, a region of interest is selected that can be monitored for actual enhancement and analyzed sufficiently before the tissue to be scanned attains a threshold enhancement level. This allows the program to use the feedback from the monitoring to enhance the accuracy of the model which is then used to predict a tissue enhancement function. The more accurate tissue enhancement function can then be used to select optimum scan parameters well before the onset of scanning.

Figure 23:
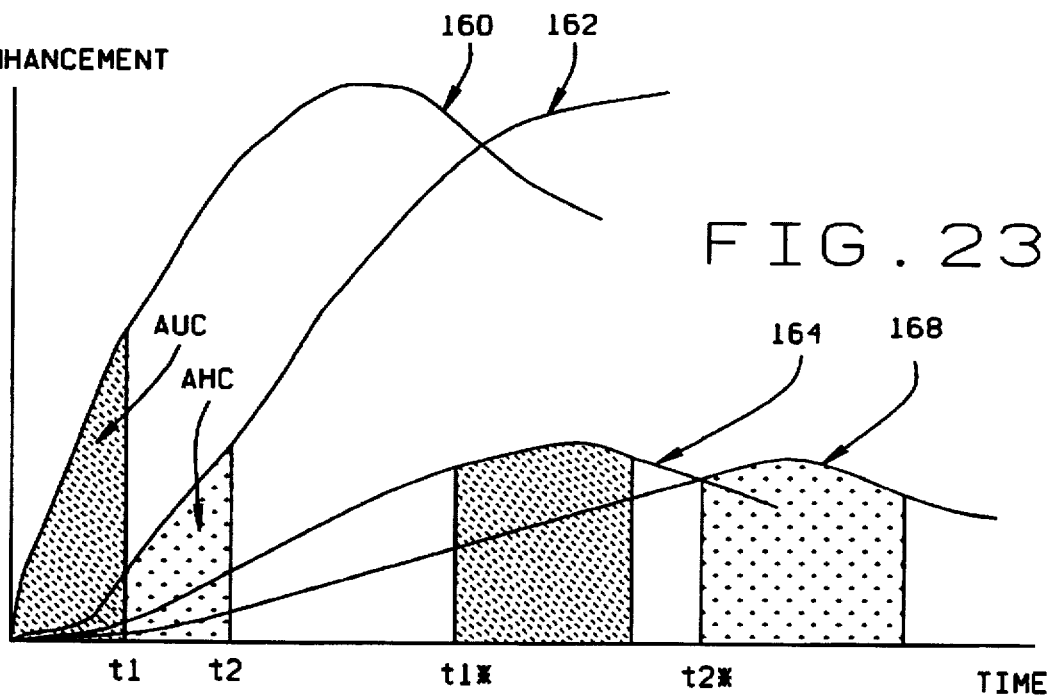
FIG. 23 is a graph showing predicted and actual aortic enhancement along with predicted and actual hepatic enhancement for a given patient.

After the operator has selected an appropriate region of interest and performed a base line scan of the region of interest, the injection is initiated according to the selected injection protocol. After the injection is initiated, and as the injection is being administered, the CT scan machine is used to monitor the region of interest enhancement level using low-dose pre-scan x-rays. The information from the pre-scan monitoring is used by the program to generate an actual aortic enhancement function as shown in FIG. 23. As in FIG. 23, the predicted 160 and actual 162 regional enhancement function can be displayed on the same graph for comparison. The data generated by the pre-scan monitoring can also be used to display the contrast enhancement level in a chart or to reconstruct an actual image of the region of interest being monitored.

After sufficient time has elapsed, the predicted regional enhancement function can be compared to the actual regional enhancement function generated by the low-dose pre-scanning of the region of interest. The results of the comparison can be used to calibrate the mathematical model for factors such as cardiac output before generating the predicted tissue enhancement level for the tissue to be scanned. Referring to FIG. 23, the predicted aortic enhancement function 160 is shown along with the actual aortic enhancement function 162 from pre-scan monitoring.

Also shown in FIG. 23 are the originally predicted hepatic enhancement function 164 and an updated or calibrated predicted hepatic enhancement function 168 corresponding to the two aortic curves. As can be seen, due to a measured decreased cardiac output in the patient, the onset of hepatic scanning must be delayed longer than originally predicted. It is this feedback that is used by the present invention to calibrate or fine tune predicted hepatic scanning based on the actual measurement of aortic enhancement levels with low-dose pre-scanning.

The slope of the measured aortic enhancement curve 162 may be calculated at a predetermined time and compared to the calculated scope of the predicted aortic enhancement curve 160 to determine the difference between the predicted and actual patient aortic output. However, this slope comparison has been unreliable as it has been observed that early action enhancement measurement is frequently pulsatile and noisy. The inventors herein have discovered that by graphing the actual enhancement as a function of time elapsed after injection (the enhancement curve 162) and measuring the area under the enhancement curve (AHC) after a predetermined time interval, this calculated AHC provides a much more reliable indicator of the patient's aortic output.

The method of the preferred embodiment plots the actual measurements of aortic enhancement to represent the actual enhancement level as a function of time and calculates the area under the curve (AHC) of the actual aortic enhancement function at a predetermined time. This ARC can compared to the area under the curve of the predicted regional enhancement function to gauge the accuracy of the model and calculate a correction factor. The present invention is very useful in determining predicted enhancement levels in specific tissue of a patient when not all of the patient specific parameters which affect transport are known. For example, as discussed above, cardiac output is a patient specific parameter which is not readily measurable. However, the differences between a predicted aortic enhancement function and an actual measured enhancement function may be analyzed to determine the cardiac output of a patient. It is known that the delay between aortic and hepatic enhancement represents the time required to distribute contrast medium from the aorta to the liver and is proportional to the cardiac output. The slower the cardiac output, the longer the delay between the time that contrast medium is delivered to the aorta and the time it is delivered to the liver. Thus, with less than standard cardiac output the onset of hepatic scanning must also be delayed so as to coincide scanning with peak enhancement.

Figure 22A:
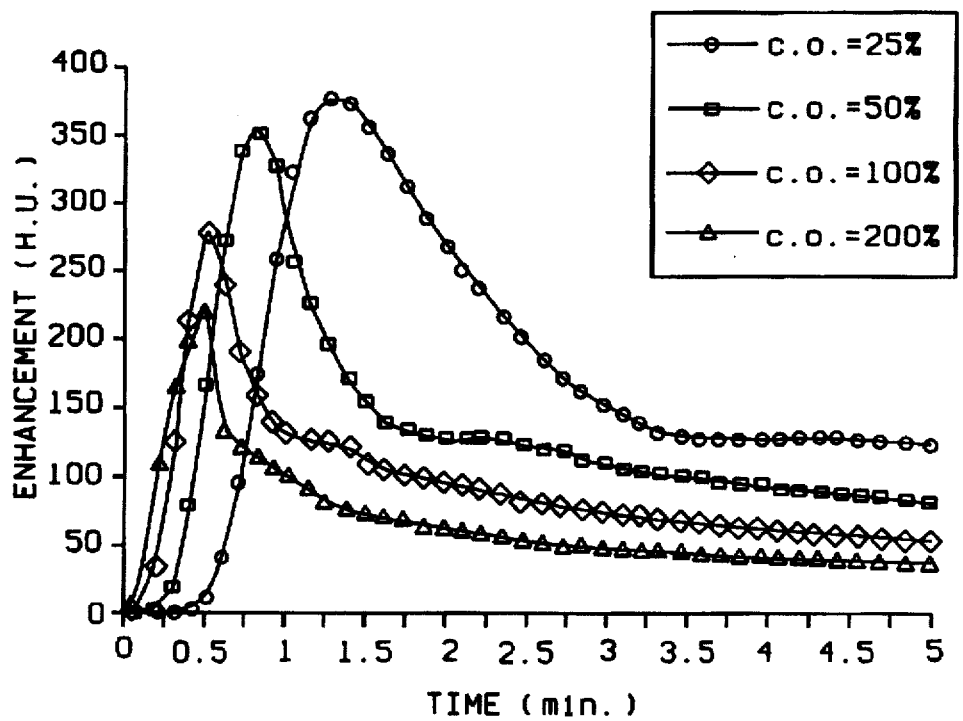
FIGS. 22A and 22B are graphs generated using the present invention showing four predicted aortic enhancement curves 22A and four different predicted hepatic enhancement curves 22B corresponding to four alternative cardiac outputs.
Figure 22B:
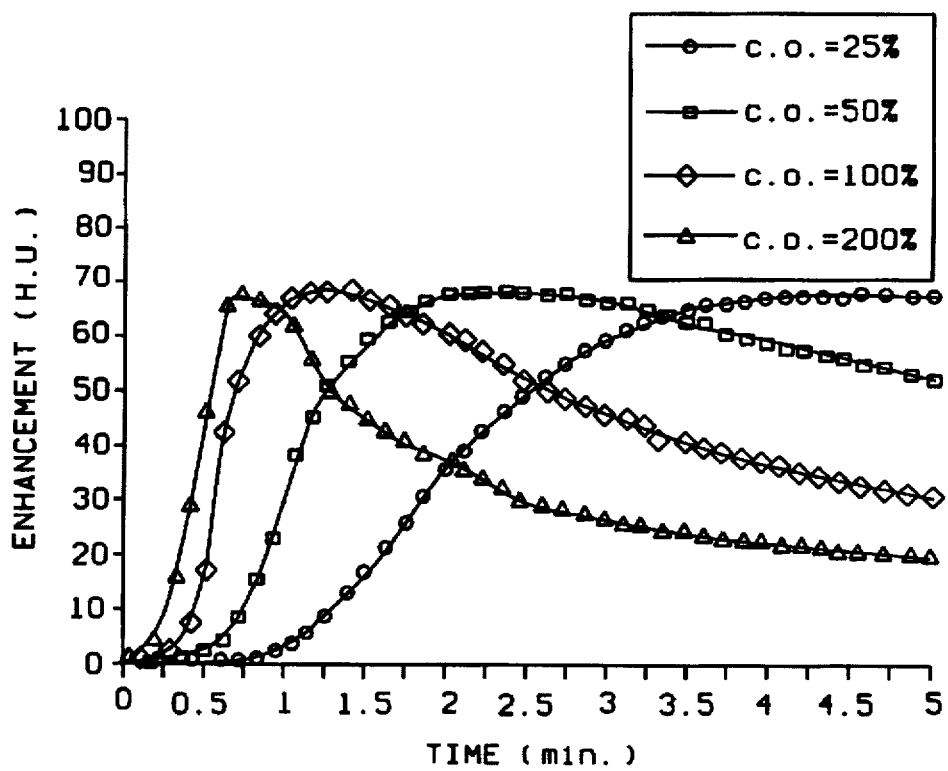

The method of the present invention was used to exhibit the effect of cardiac output on contrast enhancement for a hypothetical adult male with a fixed height (5 ft. 8 in.) and body weight (150 lbs) subjected to uniphasic-high injection protocol. The cardiac output specified for the model was varied by multiplying the standard cardiac output by 0.25, 0.50, and 2.0. Four enhancement curves were generated for predicted aortic enhancement as shown in FIG. 22(a) and four enhancement curves for predicted hepatic enhancement as shown in FIG. 22(b). As can be seen from FIG. 22(a), as the cardiac output decreases, the time delay to the peak enhancement increases in both aortic and hepatic enhancement curves. The peak aortic value increases with reduced cardiac output, while in FIG. 22(b) the plateau of peak hepatic enhancement is prolonged.

The method of the present invention is practiced as follows. A look up table can be constructed using the computer program of the present invention to generate different outputs of predicted regional enhancement levels in a region of interest based upon different cardiac outputs. An example of such a table is shown in FIG. 24. As shown in the table, predicted aortic enhancement levels are calculated at 5 second intervals for high cardiac output (200%), standard cardiac output (100%), reduced cardiac output (75%) and low cardiac output (50%). The area under the aortic curve is also calculated at intervals of 5 seconds for each different cardiac output. The last column of FIG. 24 shows an example of a list of actual aortic enhancement levels measured from low dose pre-scanning and areas under the actual regional enhancement curve for those enhancements.

A predetermined time after injection is chosen, for example 20 seconds, shown in the last column of the table in FIG. 24, the actual AHC at time equal 20 seconds is calculated. The operator (or the computer) can then compare the actual AHC at 20 seconds with the predicted AHCs in the first four columns to determine which column most accurately predicts an AHC of 776 HU*sec. at time 20 seconds. As can be seen from the table, the column having cardiac output equal to 75% most closely matches the AHC at 20 seconds (AHC=768 HU*sec). Once the cardiac output is determined in this fashion, the program can calculate a predicted hepatic enhancement function using cardiac output of 75%. This will allow the prediction of hepatic enhancement with much more accuracy because the model is more closely calibrated to the patient specific parameters which affect contrast enhancement.

The table of FIG. 20 was previously explained to determine the optimum onset of hepatic scanning for a patient with a specific body habitus and assuming a standard cardiac output. Using the results of the aortic monitoring, shown in the table of FIG. 24, a revised table was generated for the same patient. As described above, the results of the table in FIG. 24 reveal that a more accurate cardiac output for the patient is 75% of the standard. Therefore, a new table, shown in FIG. 25, was generated for predicting the optimum onset of hepatic scanning. As can be seen comparing FIG. 20 to FIG. 25, the optimum onset to hepatic scanning is changed from 60 seconds, which was predicted using standard cardiac output, to a delay of 80 seconds, predicted using cardiac output of 75% standard. The optimum scan interval is determined for the updated hepatic scanning parameters using the present invention by the greatest AHC for the interval of scan duration as discussed above. Thus, the hepatic enhancement levels can be accurately predicted to allow the entire scan duration to take place during an interval of maximum enhancement even if cardiac output cannot be readily measured.

Furthermore, the operator, or computer, has sufficient time to modify the scan parameters, such as scan delay, because the calculation of cardiac output was performed at 20 seconds after injection initiation and the onset of hepatic scanning should not occur until approximately 80 seconds after initiation of injection. Although a greater delay before calculating the area under the actual aortic enhancement curve could provide a more accurate outcome, the inventors have found that measuring aortic output at 15-20 seconds after initiation is acceptable and allows sufficient time to update the scan parameters.

Figure 26:
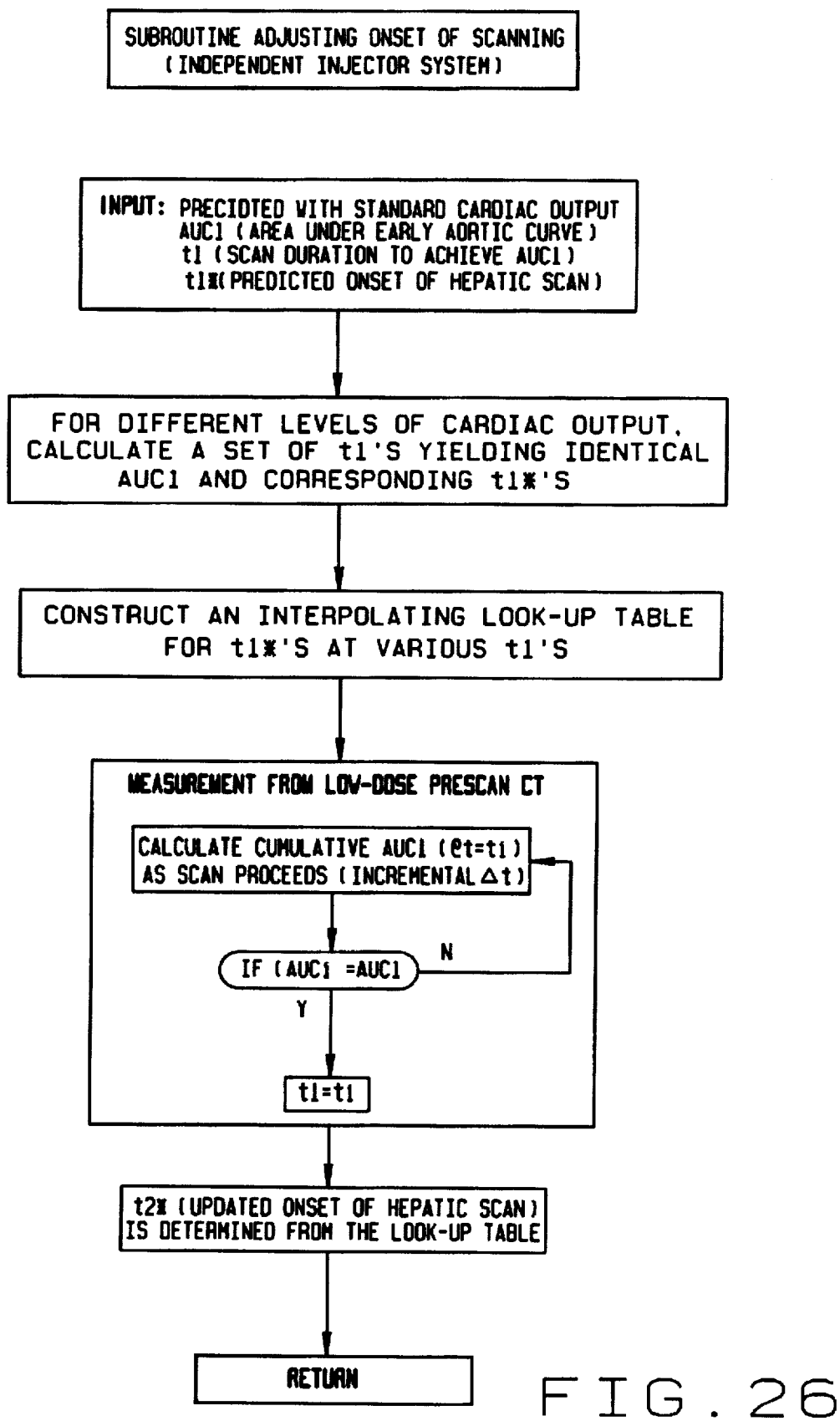
FIG. 26 is a flow chart showing the method steps of the present invention to select the optimum onset of hepatic scanning from a table of predicted optimum onset times correlated to actual measured times for the actual enhancement curve to achieve an AUC of a predetermined amount.

An alternative embodiment of the method of the present invention is shown in the flow chart of FIG. 26. This embodiment, preferably embodied in a computer program, calls for the creation of an interpolating lookup table showing the times (t1) that different cardiac outputs reach a predetermined AHC and showing predicted optimum hepatic scanning times (t1*) correlated to each (t1). The input to this embodiment is the actual level of aortic enhancement which is being attained in the patient.

The program uses the input to graph the actual enhancement function and compute at regular intervals the area under the actual enhancement curve (AHC). When the computed actual AHC is equal to the AHC from which the table was generated, the time expired after the injection initiation is recorded. The recorded time is then used with the table to find the t1 closest to the recorded time. Once the corresponding t1 is found in the table, the corresponding optimum time for onset of hepatic scanning (t1*)cis given. Using the table, the operator can thus obtain the predicted delay prior to beginning the onset of hepatic enhancement well before the time to begin the hepatic scan occurred.

There are various changes and modifications which may be made to the invention as would be apparent to those skilled in the art. However, these changes or modifications are included in the teaching of the disclosure, and it is intended that the invention be limited only by the scope of the claims appended hereto.

TABLE 1

Estimated distribution of blood in vascular system of an adult human

| Region | Volume | |
|---|---|---|
| | mL | % |
| Heart (diastolc) | 360 | 7.2 |
| Pulmonary | 440 | 8.8 |
| Arteries | 130 | 2.6 |
| Capillaries | 150 | 3.0 |
| Veins | 160 | 3.2 |

TABLE 1-continued

Estimated distribution of blood in vascular system of an adult human

| Region | Volume mL | % |
|---|---|---|
| Systemic | 4,200 | 84 |
| Aorta and large arteries | 300 | 6.0 |
| Small arteries | 400 | 8.0 |
| Capillaries | 300 | 6.0 |
| Small veins | 2,300 | 46.0 |
| Large veins | 900 | 18.0 |
| Total | 5,000 | 100 |

Modified from the reference [Milnor].

TABLE 2

Estimated distribution of cardiac output in an adult human. The liver receives dual blood supplies, hepatic artery and portal system.

| Region | Blood flow mL/min | % |
|---|---|---|
| Upper extremities | 325 | 5.0 |
| Head | 975 | 15.0 |
| Coronary | 260 | 4.0 |
| Bronchial | 130 | 2.0 |
| Kidneys | 1,430 | 22.0 |
| Liver | 1,885 | 29.0 |
| Hepatic artery | 455 | 7.0 |
| Portal | 1,430 | 22.0 |
| Spleen/stomach | 430 | 6.6 |
| Pancreas/Intestine | 1000 | 15.4 |
| Trunk/Lower Extrem. | 1,495 | 23.0 |
| Total | 6,500 | 100 |

Modified from reference [wade].

TABLE 3

Estimated distribution of body fluid in an adult human

| compartment | volume (liter) |
|---|---|
| ICF (except RBC) | 19.1 |
| ECF (except plasma) | 15.9 |
| Blood (plasma + RBC) | 5.0 |
| Total body water | 40 |

Estimation based on the volume of distribution of iohexol [Olsson].

TABLE 4

Estimated distribution of % blood flow rate and capillary volume in an adult human. Regional capillary volume is calculated proportional to a regional blood flow of the total 122% (the portal system contributes additional 22%).

| Region | Blood flow % | Capillary Volume mL |
|---|---|---|
| Upper extremities | 5.0 | 12 |
| Head | 15.0 | 37 |
| Coronary | 4.0 | 10 |
| Bronchial | 2.0 | 5 |
| Kidneys | 22.0 | 54 |
| Liver | 29.0 | 71 |
| Spleen/stomach | 6.6 | 16 |
| Pancreas/Intestine | 15.4 | 38 |
| Trunk/Lower Extrem. | 23.0 | 57 |
| Total | 100 (122) | 300 |

TABLE 5

Estimated weight water content, and fluid volume of visceral organs in a 70 Kg adult. The lung consists of 50% parenchyma and 50% non-parenchyma tissues whose capillary volumes are 150 mL and 5 mL, respectively.

| organ | weight (g) | % water | Fluid (mL) | Fluid-cap. |
|---|---|---|---|---|
| Brain | 1,450 | 76 | 1102 | 1065 |
| Heart | 300 | 79 | 237 | 227 |
| Lung | 500 + 500 | 79 | 790 | 635 |
| Kidneys | 300 | 83 | 249 | 195 |
| Liver | 1,800 | 68 | 1224 | 1153 |
| Spl./Stomach | 170/150 | 70 | 224 | 208 |
| Panc./Intest. | 60/1,770 | 70 | 1281 | 1243 |
| Total | 7,000 | | 5,107 | 4,726 |

Modified from references [ICRP, Mapleson].

TABLE 6

Tested Injection Protocols

| Protocol | First Rate (mL/sec) | First Rate Volume (mL) | Second Rate (mL/sec) | Second Rate Volume (mL) | Injection Time (sec) | Number of patient | Mean (range) of weight (lb.) |
|---|---|---|---|---|---|---|---|
| Biphasic-low | 2.5 | 50 | 1 | 75 | 95 | 28 | 158 (100–205) |
| Uniphasic-low | 2.5 | 125 | . . . | . . . | 50 | 25 | 171 (108–241) |
| Uniphasic-high | 5.0 | 125 | . . . | . . . | 25 | 27 | 177 (98–300) |

What is claimed is:

1. A method of determining a set of parameters for an injection protocol for scanning a tissue in a patient using computed tomography, the patient having a plurality of patient specific parameters, wherein the tissue to be scanned is enhanced with an intravascularly injected contrast agent, comprising the steps of:

generating a tissue enhancement function comprising a tissue enhancement level for the tissue to be scanned as a function of an elapsed time after injection based on the patient specific parameters and a specified injection protocol; and determining the set of injection protocol parameters for an optimum scan based on the predicted tissue enhancement function.

2. The method of claim 1 wherein the step of determining the set of parameters for an optimum scan includes using the predicted tissue enhancement function to thereby determine an injection flow rate and a contrast volume which is predicted to cause the tissue enhancement level to exceed a pre-selected threshold value.

3. The method of claim 2 further comprising the step of adjusting the set of parameters until the tissue enhancement level is predicted to exceed the threshold value.

4. The method of claim 3 wherein the set of parameters is sequentially adjusted until the predicted tissue enhancement function is maintained above the threshold value for a time period at least approximately equal to a specified scan duration.

5. The method of claim 4 wherein the step of adjusting the set of parameters includes selecting the injection flow rate and selecting the injection volume.

6. The method of claim 1 wherein the step of determining a set of parameters for an optimum scan includes determining an optimum scan interval equal to a specified scan duration during which the predicted tissue enhancement function is the greatest.

7. The method of claim 6 wherein the step of determining the optimum scan interval includes integrating the predicted enhancement function for successive intervals equal to the specified scan duration and selecting an interval having the greatest integration value as the optimum scan interval.

8. The method of claim 1, further comprising the steps of:

predicting prior to injecting the contrast agent a regional enhancement level as a function of an elapsed time after injection for a region of interest in the patient based on the patient specific parameters and specified injection protocol;

initiating the injection protocol;

sequentially measuring an actual enhancement level in the region of interest at predetermined elapsed times after initiating the injection to generate an actual regional enhancement function;

calculating a correction factor based on the relationship between the predicted regional enhancement function and the actual regional enhancement function; and using the correction factor to calibrate the predicted tissue enhancement function.

9. The method of claim 8 wherein at least one of the plurality of patient specific parameters has an unknown value and wherein the step of predicting a regional enhancement function includes the steps of:

providing a mathematical model of a cardiovascular system, the model mathematically describing transport of the contrast agent through the cardiovascular system;

inputting a plurality of alternatives for the unknown patient parameter into the model to generate a set of alternative regional enhancement functions with the set comprising a member for each alternative; and selecting a predicted regional enhancement function from the set of alternative regional enhancement functions.

10. The method of claim 9 wherein the step of selecting a predicted regional enhancement function from the set of alternative regional enhancement functions comprises the steps of:

comparing the actual regional enhancement function to the members of the set of alternative regional enhancement functions; and selecting from the set of alternative regional enhancement functions the member which most closely resembles the actual enhancement function.

11. The method of claim 10 wherein the step of selecting the member from the set of alternative regional enhancement functions includes the steps of:

graphing the members of the set of alternative regional enhancement functions;

graphing the actual regional enhancement function;

integrating the actual regional enhancement graph from start to a predetermined time after injection;

determining which member of the alternative regional enhancement graphs at the predetermined time has an integrated area closest to the integrated area of the actual regional enhancement graph at the predetermined time.

12. The method of claim 9 wherein the tissue to be scanned is distinct from the region of interest and wherein the step of using the correction factor to calibrate the predicted tissue enhancement function includes the steps of:

inputting into the mathematical model the alternative chosen for the unknown patient parameter which was used to generate the predicted regional enhancement function; and generating a revised predicted tissue enhancement function.

13. The method of claim 12 wherein the step of determining a set of parameters for an optimum scan includes the step of:

using the revised predicted tissue enhancement function to determine an optimum scan delay to cause the onset of the scanning of the tissue to coincide with a threshold enhancement level in the tissue.

14. The method of claim 8 wherein the step of sequentially measuring an actual enhancement level is performed using low-dose pre-scanning of the region of interest.

15. The method of claim 9 wherein the region of interest is the tissue to be scanned.

16. The method of claim 9 wherein said mathematical model is embodied in a computer program.

17. A contrast injector system comprising:

a contrast injector;

a computer having a memory connected to said contrast injector for controlling its operation; and a computer program in said computer memory, said computer program having means for predicting a structure specific CT enhancement level in a patient having a specific patient habitus based on a specified injection protocol.

18. The contrast injector of claim 17, wherein said computer program comprises:

means for predicting prior to implementing the injection protocol a tissue enhancement level as a function of elapsed time based on the injection protocol and the specific patient habitus; and means for determining an optimum injection flow rate and an optimum contrast volume based on the predicted tissue enhancement level.

19. The contrast injector of claim 18 wherein the computer program further comprises:
means for accepting an input including a revised injection rate and a revised contrast volume;
means for revising the predicted tissue enhancement level based on the revised injection flow rate and the revised contrast volume.

20. The contrast injector of claim 19 wherein the computer program includes means for implementing the injection protocol using the revised injection flow rate and revised contrast volume.

21. The contrast injector of claim 20 wherein the contrast injector is in communication with a computed tomography machine and wherein the computer program includes means for signaling the computed tomography machine to perform a scan.

22. A computed tomography system for scanning a tissue in a patient, the patient having a plurality of patient specific parameters, wherein the tissue to be scanned is enhanced with an intravascularly injected contrast agent, the system comprising:
a computed tomography machine;
an injector system in communication with the computed tomography machine;
a computer having a memory, the computer in communication with both the injector system and the computed tomography machine for coordinating their operation; and
a computer program in the computer memory, the computer program having means for predicting prior to injecting the contrast agent a tissue enhancement level for the tissue based on the patient specific parameters and a selected injection protocol.

23. The system of claim 22 wherein the computer program includes:
means for determining an optimum injection protocol for injection of the contrast agent; and
means for implementing the optimum injection protocol.

24. The system of claim 22 further comprising means for monitoring actual regional enhancement levels in a region of interest in the patient after initiation of the injection protocol.

25. The system of claim 24 wherein the computer program includes means for receiving and analyzing the regional enhancement levels to thereby confirm the predicted tissue enhancement level.

26. The system of claim 25 wherein the computer program includes means for revising the predicted tissue enhancement level based on the regional enhancement level.

27. A computer being programmed for predicting a structure specific CT enhancement level in a patient for a given patient habitus and a specific contrast injection protocol comprising:
a computer having a memory;
a computer program in said memory, the program having means for accepting patient specific information and contrast specific information which affect physiological parameters of contrast enhancement and means for computing and outputting structure specific enhancement levels as a function of an elapsed time after injection.

28. The computer of claim 27 wherein the computer program further comprises:

means for optimizing the injection protocol to thereby cause at least a threshold contrast enhancement level over a predetermined scan duration; and
means for communicating the optimum injection protocol to an injector.

29. The computer of claim 27 wherein the computer program includes:
means for determining a set of scan parameters for an optimum scan based on the computed enhancement levels;
means for communicating the set of scan parameters to a CT scan machine.

30. The computer of claim 27 wherein the computer program includes means for monitoring actual enhancement levels in a region of interest to thereby confirm the computed enhancement levels.

31. A method for determining an injection protocol for injecting a contrast agent into a patient for enhancing a tissue desired to be scanned with computed tomography, the method comprising the steps of:
generating a plurality of predicted tissue enhancement functions based on different patient parameters; and
selecting one of said predicted tissue enhancement functions as being close to expected based upon feedback from a low dose scan of a region of interest.

32. The method of claim 31 wherein the selecting step includes the steps of generating from said low dose scan an actual tissue enhancement function of said region of interest, integrating said actual tissue enhancement function over a predetermined time period, comparing said integrated value with corresponding integrated values for each of the predicted tissue enhancement functions and selecting as desired the predicted tissue enhancement function with the closest integrated value.

33. The method of claim 32 further comprising the steps of determining a patient parameter based upon the selected predicted tissue enhancement function, and determining a predicted tissue enhancement function for the tissue to be scanned based at least in part on said determined patient parameter.

34. The method of claim 31 wherein the low dose scan is of a tissue different than the tissue desired to be scanned.

35. A method for determining an injection protocol for injecting a contrast agent into a patient for enhancing a tissue desired to be scanned with computed tomography, the method comprising the steps of:
generating a predicted tissue enhancement function;
selecting a threshold level; and
adjusting the injection protocol until the tissue enhancement function remains greater than the threshold level for a time period at least equal to a desired scan duration.

36. The method of claim 35 further comprising the steps of determining an optimal scan start time and end time by integrating the tissue enhancement function for successive scan duration intervals contained within the portion wherein the threshold is exceeded, and choosing as optimal the integrated interval having the greatest value.

37. The method of claim 31 further comprising the steps of implementing said method in a computer, and performing a CT scan using said determined injection protocol.

38. The method of claim 35 further comprising the steps of implementing said method in a computer, and performing a CT scan using said determined injection protocol.

* * * * *